United States Patent
Keer

(10) Patent No.: US 8,920,800 B2
(45) Date of Patent: *Dec. 30, 2014

(54) TREATMENT OF CANCER WITH ELEVATED DOSAGES OF SOLUBLE FGFR1 FUSION PROTEINS

(71) Applicant: Five Prime Therapeutics, Inc., South San Francisco, CA (US)

(72) Inventor: Harold Keer, Redwood City, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/913,292

(22) Filed: Jun. 7, 2013

(65) Prior Publication Data

US 2014/0056891 A1    Feb. 27, 2014

Related U.S. Application Data

(63) Continuation of application No. 13/296,161, filed on Nov. 14, 2011, now Pat. No. 8,481,038.

(60) Provisional application No. 61/413,940, filed on Nov. 15, 2010.

(51) Int. Cl.
| | | |
|---|---|---|
| *A61K 39/00* | (2006.01) | |
| *A61K 38/00* | (2006.01) | |
| *A61P 35/00* | (2006.01) | |
| *A61K 39/395* | (2006.01) | |
| *A61K 38/17* | (2006.01) | |
| *A61K 45/06* | (2006.01) | |

(52) U.S. Cl.
CPC ........... *A61K 39/3955* (2013.01); *A61K 38/179* (2013.01); *A61K 45/06* (2013.01); *C07K 2319/30* (2013.01)
USPC ...................................... 424/134.1; 514/19.3

(58) Field of Classification Search
CPC .... C07K 14/47; C07K 14/71; C07K 2319/32; A61K 45/06; A61K 31/00; A61K 31/7115
See application file for complete search history.

(56) References Cited

U.S. PATENT DOCUMENTS

| | | | |
|---|---|---|---|
| 5,229,501 A | 7/1993 | Keifer et al. | |
| 5,288,855 A | 2/1994 | Bergonzoni et al. | |
| 5,474,914 A | 12/1995 | Spaete | |
| 5,486,462 A | 1/1996 | Rutter et al. | |
| 5,707,632 A | 1/1998 | Williams et al. | |
| 5,750,371 A | 5/1998 | Senoo et al. | |
| 5,767,250 A | 6/1998 | Spaete | |
| 5,863,888 A | 1/1999 | Dionne et al. | |
| 6,255,454 B1 | 7/2001 | Keifer et al. | |
| 6,344,546 B1 | 2/2002 | Dionne et al. | |
| 6,350,593 B1 | 2/2002 | Williams et al. | |
| 6,355,440 B1 | 3/2002 | Williams et al. | |
| 6,384,191 B1 | 5/2002 | Williams et al. | |
| 6,517,872 B1 | 2/2003 | Yayon et al. | |
| 6,656,728 B1 | 12/2003 | Kavanaugh et al. | |
| 6,844,168 B1 | 1/2005 | Keifer et al. | |
| 7,135,311 B1 | 11/2006 | David et al. | |
| 7,297,493 B2 | 11/2007 | Lorenzi et al. | |
| 7,297,774 B2 | 11/2007 | Ullrich et al. | |
| 7,645,609 B2 | 1/2010 | Follstad | |
| 7,678,890 B2 | 3/2010 | Bosch et al. | |
| 7,947,811 B2 | 5/2011 | Pereira et al. | |
| 7,982,014 B2 | 7/2011 | Williams et al. | |
| 8,119,770 B2 | 2/2012 | Blanche et al. | |
| 8,173,134 B2 | 5/2012 | Bosch et al. | |
| 8,338,569 B2 | 12/2012 | Marshall et al. | |
| 8,481,038 B2 | 7/2013 | Keer | |
| 2004/0063910 A1 | 4/2004 | Kavanaugh et al. | |
| 2004/0115768 A1 | 6/2004 | Follstad | |
| 2005/0187150 A1 | 8/2005 | Mohammadi et al. | |
| 2006/0234347 A1 | 10/2006 | Harding et al. | |
| 2006/0286102 A1 | 12/2006 | Jin et al. | |
| 2007/0248604 A1 | 10/2007 | Desnoyers et al. | |
| 2007/0248605 A1 | 10/2007 | Hestir et al. | |
| 2008/0171689 A1 | 7/2008 | Williams et al. | |
| 2010/0111873 A1 | 5/2010 | Russell et al. | |
| 2012/0128672 A1 | 5/2012 | Keer | |
| 2012/0183541 A1 | 7/2012 | Brennan et al. | |

(Continued)

FOREIGN PATENT DOCUMENTS

| | | |
|---|---|---|
| EP | 0 545 343 A1 | 6/1993 |
| EP | 1910542 B2 | 2/2009 |

(Continued)

OTHER PUBLICATIONS

Adam et al., "Toward optimized front-line therapeutic strategies in patients with metastatic colorectal cancer—an expert review from the International Congress on Anti-cancer Treatment (ICACT) 2009," Annals of Oncology, 21: 1579-1584 (2010).

Akimoto et al., "Fibroblast growth factor 2 promotes microvessel formation from mouse embryonic aorta" Am. J. Physiol. Cell Physiol., vol. 284, No. 2, 2003, pp. C371-C377.

Anderson et al., "Apert syndrome mutations in fibroblast growth factor receptor 2 exhibit increased affinity for FGF ligand" Human Molecular Genetics, vol. 7, No. 9, 1998, pp. 1475-1483.

Andre et al., "Molecular Characterization of Breast Cancer with High-Resolution Oligonucleotide Comparative Genomic Hybridization Array," Clin Cancer Res, 2009, 15(2): 441-451.

(Continued)

*Primary Examiner* — Robert Landsman
(74) *Attorney, Agent, or Firm* — Casimir Jones, S.C.

(57) ABSTRACT

The present invention provides methods of treating a patient having a cancer comprising administering to the patient a soluble Fibroblast Growth Factor Receptor 1 (FGFR1) fusion protein such as an extracellular domain of an FGFR1 polypeptide linked to an Fc polypeptide or another fusion partner. The fusion protein may be administered at a dose of at least about 2 mg/kg body weight. In some embodiments, the patient has a fibroblast growth factor-2 (FGF-2) plasma concentration of at least 6 pg/ml. In some embodiments, the cancer is characterized by a Fibroblast Growth Factor Receptor 2 (FGFR2) having a ligand-dependent activating mutation.

31 Claims, 3 Drawing Sheets

(56) References Cited

U.S. PATENT DOCUMENTS

| | | |
|---|---|---|
| 2012/0237511 A1 | 9/2012 | Long et al. |
| 2012/0251538 A1 | 10/2012 | Harding et al. |
| 2012/0301921 A1 | 11/2012 | Williams et al. |
| 2013/0004492 A1 | 1/2013 | Marshall et al. |
| 2013/0316740 A1 | 11/2013 | Scarafia et al. |

FOREIGN PATENT DOCUMENTS

| | | |
|---|---|---|
| EP | 2083081 A1 | 7/2009 |
| WO | WO 91/00916 | 1/1991 |
| WO | WO 91/11459 | 8/1991 |
| WO | WO 02/094852 | 11/2002 |
| WO | WO 2004/110487 A1 | 12/2004 |
| WO | WO 2005/113596 A2 | 12/2005 |
| WO | WO 2005/115363 A2 | 12/2005 |
| WO | WO 2006/081430 A2 | 8/2006 |
| WO | WO 2006/113277 A2 | 10/2006 |
| WO | WO 2007/014123 A2 | 2/2007 |
| WO | WO 2007/059574 A1 | 5/2007 |
| WO | WO 2007/134210 A2 | 11/2007 |
| WO | WO 2008/065543 A2 | 6/2008 |
| WO | WO 2008/118877 A2 | 10/2008 |
| WO | WO 2008/133873 | 11/2008 |
| WO | WO 2010/017198 | 2/2010 |
| WO | WO 2011/034940 | 3/2011 |
| WO | WO 2011/060333 A1 | 5/2011 |
| WO | WO 2011/084711 | 7/2011 |
| WO | WO 2012/125812 | 9/2012 |
| WO | WO 2012/177481 | 12/2012 |
| WO | WO 2013/074492 | 5/2013 |

OTHER PUBLICATIONS

Auguste et al., "Inhibition of fibroblast growth factor-fibroblast growth factor receptor activity in glioma cells impedes tumor growth by both angiogenesis-dependent and -independent mechanisms" Cancer Research, vol. 61, Feb. 15, 2001, pp. 1717-1726.
Baker et al., "Metabolic control of recombinant protein N-glycan processing in NS0 and CHO cells" Biotechnology and Bioengineering, vol. 73, No. 3, May 5, 2001, pp. 188-202.
Ballinger et al., "Semirational design of a potent, artificial agonist of fibroblast growth factor receptors" Nature Biotechnology, vol. 17, Dec. 1999, pp. 1199-1204.
Bansal et al., "The Molecular Biology of Endometrial Cancers and the Implications for Pathogenesis, Classification, and Targeted Therapies," Cancer Control, 2009, 16(1):8-13.
Bass et al., "SOX2 Is an Amplified Lineage Survival Oncogene in Lung and Esophageal Squamous Cell Carcinomas," Nat. Genet., 2009, 41(11): 1238-1242, including supplemental information (15 pages).
Beroukhim et al., "The landscape of somatic copy-number alteration across human cancers," Nature, 2010, 463: 899-905.
Bjornsson et al., Pharmacokinetics of Heparin. II. Studies of Time Dependence in Rats, the Journal of Pharmacology and Experimental Therapeutics, vol. 210, No. 2, Apr. 1979, pp. 243-246.
Byron and Pollock, "FGFR2 as a molecular target in endometrial cancer," Future Oncol, 2009, 5(1):27-32.
Byron et al., "Inhibition of Activated Fibroblast Growth Factor Receptor 2 in Endometrial Cancer Cells Induces Cell Death Despite PTEN Abrogation," Cancer Res, 2008, 68(17):6902-6907.
Byron et al., "FGFR2 mutations are rare across histologic subtypes of ovarian cancer," Gynecologic Oncology, 2010, 117(1):125-129.
Celli et al., "Soluble dominant-negative receptor uncovers essential roles for fibroblast growth factors in multi-organ induction and patterning" The EMBO Journal, vol. 17, No. 6, Mar. 16, 1998, pp. 1642-1655.
Chellaiah et al., "Mapping ligand binding domains in chimeric fibroblast growth factor receptor molecules" J. Biol. Chem., vol. 274, No. 49, Dec. 3, 1999, pp. 34785-34794.
Cheon et al., "High-affinity binding sites for related fibroblast growth factor ligands reside within different receptor immunoglobulin-like domains" Proc. Natl. Acad. Sci., vol. 91, Feb. 1994, pp. 989-993.

Choo et al., SPdb—a Signal Peptide Database, BMC Bioinformatics, vol. 6, No. 249, Oct. 2005, pp. 1-8.
Compagni et al., "Fibroblast growth factors are required for efficient tumor angiogenesis" Cancer Research, vol. 60, Dec. 15, 2000, pp. 7163-7169.
Coughlin et al., "Acidic and basic fibroblast growth factors stimulate tyrosine kinase activity in vivo" J. Biol. Chem., vol. 263, No. 2, Jan. 15, 1988, pp. 988-993.
Courjal et al., "Comparative Genomic Hybridization Analysis of Breast Tumors with Predetermined Profiles of DNA Amplification," Cancer Res. 1997, 57(19):4368-77.
Cuny et al., "Relating genotype and phenotype in breast cancer: an analysis of the prognostic significance of amplification at eight different genes or loci and of p53 mutations," Cancer Res. 2000; 60(4):1077-83.
Dutt et al., "Drug-sensitive FGFR2 mutations in endometrial carcinoma," PNAS, 2008, 105(25):8713-8717.
Dutt et al., "Inhibitor-Sensitive FGFR1 Amplification in Human Non-Small Cell Lung Cancer," 2011, PLoS ONE, 6(6): e20351, 10 pages.
Elbauomy Elsheikh et al., "FGFR1 amplification in breast carcinomas: a chromogenic in situ hybridisation analysis," Breast Cancer Research 2007, 9:R23, 12 pages.
Ezzat et al., "A soluble dominant negative fibroblast growth factor receptor 4 isoform in human MCF-7 breast cancer cells" Biochem. Biophys. Res. Comm., vol. 287, No. 1, 2001, pp. 60-65.
Feige et al., "Glycosylation of the basic fibroblast growth factor receptor" J. Biol. Chem., vol. 263, No. 28, Oct. 5, 1988, pp. 14023-14029.
Gatius et al., "FGFR2 alterations in endometrial carcinoma," Modern Pathology, 2011, 24:1500-1510.
Gelsi-Boyer et al., "Comprehensive Profiling of 8p11-12 Amplification in Breast Cancer," Mol Cancer Res 2005;3(12): 655-667.
Genbank Accession No. X76885, 1994, 2 pages.
Genbank Accession No. Q90330, Nov. 1, 1996, 6 pages.
Gowardhan et al., "Evaluation of the fibroblast growth factor system as a potential target for therapy in human prostate cancer" British Journal of Cancer, vol. 92, Jan. 18, 2005, pp. 320-327.
Grossman et al., "Expression of human thyrotropin in cell lines with different glycosylation patterns combined with mutagenesis of specific glycosylation sites" J. Biol. Chem., vol. 270, No. 49, Dec. 8, 1995, pp. 29378-29385.
Guillonneau et al., "Fibroblast growth factor (FGF) soluble receptor 1 acts as a natural inhibitor of FGF2 neurotrophic activity during retinal degeneration" Molecular Biology of the Cell, vol. 9, Oct. 1998, pp. 2785-2802.
Hanneken et al., "Identification of soluble forms of the fibroblast growth factor receptor in blood" Proc. Natl. Acad. Sci., vol. 91, Sep. 1994, pp. 9170-9174.
Hanneken et al., "Soluble forms of the high-affinity fibroblast growth factor receptor in human vitreous fluid" Investigative Opthalmology & Visual Science, vol. 36, No. 6, May 1995, pp. 1192-1196.
Hanneken et al., "Structural characterization of the circulating soluble FGF receptors reveals multiple isoforms generated by secretion and ectodomain shedding" FEBS Letters, vol. 489, 2001, pp. 176-181.
Harding et al., "Role of VEGF, PDGF and FGF in glioblastoma progression as determined by soluble decoy receptor expression in preclinical models" Cell Genesys, Inc., Abstract No. 3030, presented at the AACR Annual Meeting, Apr. 16-20, 2005, 1 page.
Harding et al., "Preclinical Efficacy of FP-1039 (FGFR1:Fc) in Endometrical Carcinoma Models with Activating Mutations in FGFR2," AACR 101st Annual Meeting Poster (Apr. 17-21, 2010).
Harding et al., "Preclinical efficacy of fibroblast growth factor ligand trap HGS1036 in lung carcinoma models with genomic amplification of FGFR1" Poster from AACR Annual Meeting, Mar. 31-Apr. 4, 2012. 1 page.
Harding et al., "Blockade of Nonhormonal Fibroblast Growth Factors by FP-1039 Inhibits Growth of Multiple Types of Cancer," Science Translational Medicine, Mar. 2013, 5:178ra39 , pp. 1-9.
Harding et al., "Blockade of Nonhormonal Fibroblast Growth Factors by FP-1039 Inhibits Growth of Multiple Types of Cancer," Sci Transl Med, 2013, 5:178ra39, Supplemental Materials, 28 pages.

(56) References Cited

OTHER PUBLICATIONS

Ibrahimi et al., "Structural basis for fibroblast growth factor receptor 2 activation in Apert syndrome," PNAS, 2001, 98(13):7182-7187.
Ibrahimi et al., "Biochemical analysis of pathogenic ligand-dependent FGFR2 mutations suggests distinct pathophysiological mechanisms for craniofacial, and limb abnormalities," Human Molecular Genetics, 2004, 13(19):2313-2324.
Ibrahimi et al., "Proline to arginine mutations in FGF receptors 1 and 3 result in Pfeiffer and Muenke craniosynostosis syndromes through enhancement of FGF binding affinity," Hum. Mol. Genet., 13: 69-78 (2004).
Ibrahimi et al., "Analysis of Mutations in Fibroblast Growth Factor (FGF) and a Pathogenic Mutation in FGF Receptor (FGFR) Provides Direct Evidence for the Symmetric Two-End Model for FGFR Dimerization," Mol. Cell. Biol., 25(2): 671-684 (2005).
Jang et al., "FGFR1 is amplified during the progression of in situ to invasive breast carcinoma," Breast Cancer Research, 2012, 14:R115, pp. 1-12.
Johnson et al., "Diverse forms of a receptor for acidic and basic fibroblast growth factors" Molecular and Cellular Biology, vol. 10, No. 9, Sep. 1990, pp. 4728-4736.
Johnson et al, "The human fibroblast growth factor receptor genes: a common structural arrangement underlies the mechanisms for generating receptor forms that differ in their third immunoglobulin domain" Molecular and Cellular Biology, vol. 11, No. 9, Sep. 1991, pp. 4627-4634.
Kan et al., "Divalent cations and heparin-heparan sulfate cooperate to control assembly and activity of the fibroblast growth factor receptor complex" J. Biol. Chem., vol. 271, No. 42, Oct. 18, 1996, pp. 26143-26148.
Katoh, "Cancer genomics and genetics of FGFR2 (Review)," International Journal of Oncology, 2008, 33:233-237.
Katoh, "FGFR2 Abnormalities Underlie a Spectrum of Bone, Skin, and Cancer Pathologies," Journal of Investigative Dermatology, 2009, 129:1861-1867.
Kaufman et al., "Characterization of ligand binding to immobilized biotinylated extracellular domains of three growth factor receptors" Anal. Biochem., vol. 211, No. 2, Jun. 1993, pp. 261-266.
Keer et al., "Enrolling a Rare Patient Population: Establishing Proof of Concept for FP-1039, an FGF 'Trap,' in Endometrial Cancer Patients with the S252W FGFR2 Mutation," American Society of Clinical Oncology 2010, Annual Meeting, Jun. 4-8, 2010, Chicago, IL.
Keifer et al., "Molecular cloning of a human basic fibroblast growth factor receptor cDNA and expression of a biologically active extracellular domain in a baculovirus system" Growth Factors, vol. 5, 1991, pp. 115-127.
Kleeff et al., "Adenovirus-mediated transfer of a truncated fibroblast growth factor (FGF) type I receptor blocks FGF-2 signaling in multiple pancreatic cancer cell lines" Pancreas, vol. 28, No. 1, Jan. 2004, pp. 25-30.
Knights & Cook, "De-regulated FGF receptors as therapeutic targets in cancer," Pharmacol Ther, 2010, 125(1):105-117.
Kwabi-Addo et al., "The role of fibroblast growth factors and their receptors in prostate cancer" Endocrine-Related Cancer, vol. 11, No. 4, Dec. 2004, pp. 709-724.
Lazar et al., "Transforming Growth Factor alpha: Mutation of Aspartic Acid 47 and Leucine 48 Results Different Biological Activities," Mol Cell Biol, 1988, 8(3):1247-1252.
Lee et al., "Purification and complementary DNA cloning of a receptor for basic fibroblast growth factor" Science, vol. 245, No. 4913, Jul. 7, 1989, pp. 57-60.
Lee et al., "Molecular profiles of EGFR, K-ras, c-met, and FGFR in pulmonary pleomorphic carcinoma, a rare lung malignancy," J. Cancer Res. Clin. Oncol., May 28, 2011, 9 pages.
Levi et al., "Matrix metalloproteinase 2 releases active soluble ectodomain of fibroblast growth factor receptor 1", XP-002413740, Proc. Natl. Acad. Sci., USA, vol. 93, pp. 7069-7074, (Jul. 1996).

Li et al., "Cell transformation by fibroblast growth factors can be suppressed by truncated fibroblast growth factor receptors" Molecular and Cellular Biology, vol. 14, No. 11, Nov. 1994, pp. 7660-7669.
Liu et al, "Utilization of Unlabeled Probes for the Detection of Fibroblast Growth Factor Receptor 2 Exons 7 and 12 Mutations in Endometrial Carcinoma," Appl Immunohistochem Mol Morphol, 2011, 19(4):341-346.
Liuzzo et al., "Human leukemia cell lines bind basic fibroblast growth factor (FGF) on FGF receptors and heparin sulfates: downmodulation of FGF receptors by phorbol ester" Blood, vol. 87, No. 1, Jan. 1, 1996, pp. 245-255.
Long et al. "Abstract #2789: Antitumor efficacy of FP-1039, a soluble FGF receptor 1:Fc conjugate, as a single agent or in combination with anticancer drugs," Proceedings of the American Association for Cancer Research, Apr. 18-22, 2009 Denver, CO.
Long et al. "Preclinical antitumor efficacy of FP-1039, a soluble FGF receptor 1:Fc conjugate, as a single agent or in combination with anticancer drugs," Proceedings of the American association for Cancer Research, Apr. 17-22, 2009 Denver, CO.
Loo et al., "Production and characterization of the extracellular domain of recombinant human fibroblast growth factor receptor 4," Intl. J. Biochem. Cell Biol., 32: 489-497 (2000).
Lopez et al., "A novel type I fibroblast growth factor receptor activates mitogenic signaling in the absence of detectable tyrosine phosphorylation of FRS2" J. Biol. Chem., vol. 275, No. 21, May 26, 2000, pp. 15933-15939.
Lundin et al., "Selectively desulfated heparin inhibits fibroblast growth factor-induced mitogenicity and angiogenesis" J. Biol. Chem., vol. 275, No. 32, Aug. 11, 2000, pp. 24653-24660.
Ma et al., "Combination of antiangiogenesis with chemotherapy for more effective cancer treatment," Mol Cancer Ther, 7: 3670-3684 (2008).
Mansukhani et al., "A murine fibroblast growth factor (FGF) receptor expressed in CHO cells is activated by basic FGF and Kaposi FGF" Proc. Natl. Acad. Sci., vol. 87, Jun. 1990, pp. 4378-4382.
Marics et al., "FGFR4 signaling is a necessary step in limb muscle differentiation," Development, 2002, 129:4559-4569.
Marshall et al., "Fibroblast Growth Factor Receptors Are Components of Autocrine Signaling Networks in Head and Neck Squamous Cell Carcinoma Cells," 2011, 17(15): 5016-5025.
Mayer et al., "Ratiometric dosing of anticancer drug combinations: Controlling drug ratios after systemic administration regulates therapeutic activity in tumor-bearing mice," Mol Cancer Ther, 5(7): 1854-1863 (2006).
Meijer et al., Fibroblast Growth Factor Receptor 4 Predicts Failure on Tamoxifen Therapy in Patients with Recurrent Breast Cancer, Endocrine-Related Cancer, vol. 15, 2008, pp. 101-111.
Moloney et al., "Exclusive paternal origin of new mutations in Apert syndrome," Nature Genetics, 1996, 13:48-53.
Ogawa et al., "Anti-tumor angiogenesis therapy using soluble receptors: enhanced inhibition of tumor growth when soluble fibroblast growth factor receptor-1 is used with soluble vascular endothelial growth factor receptor" Cancer Gene Therapy, vol. 9, Aug. 2002, pp. 633-640.
Olsen et al., "Insights into the molecular basis for fibroblast growth factor receptor autoinhibition and ligand-binding promiscuity" Proc. Natl. Acad. Sci., vol. 101, No. 4 Jan. 27, 2004, pp. 935-940.
Ornitz et al., "Heparin is required for cell-free binding of basic fibroblast growth factor to a soluble receptor and for mitogenesis in whole cells" Molecular and Cellular Biology, vol. 12, Jan. 1992, pp. 240-247.
Ornitz et al., "Receptor specificity of the fibroblast growth factor family" J. Biol. Chem., vol. 271, No. 25, Jun. 21, 1996, pp. 15292-15297.
Otto et al., "Sialylated complex-type N-glycans enhance the signaling activity of soluble intercellular adhesion molecule-1 in mouse astrocytes" J. Biol. Chem., vol. 279, No. 34, Aug. 20, 2004, pp. 35201-35209.
Pasquale et al., "Identification of a developmentally regulated protein-tyrosine kinase by using anti-phosphotyrosine antibodies to screen a cDNA expression library" Proc. Natl. Acad. Sci., vol. 86, Jul. 1989, pp. 5449-5453.

(56) References Cited

OTHER PUBLICATIONS

Pellegrini et al., "Crystal structure of fibroblast growth factor receptor ectodomain bound to ligand and heparin," Nature, 407: 1029-1034 (2000).
Plotnikov et al., "Structural basis for FGF receptor dimerization and activation" Cell, vol. 98, Sep. 3, 1999, pp. 641-650.
Plotnikov et al., "Crystal structures of two FGF-FGFR complexes reveal the determinants of ligand-receptor specificity" Cell, vol. 101, May 12, 2000, pp. 413-424.
Pollock et al., "Frequent activating FGFR2 mutations in endometrial carcinomas parallel germline mutations associated with craniosynostosis and skeletal dysplasia syndromes," Oncogene, 2007, 26:7158-7162.
Powell et al., "Fibroblast growth factor receptors 1 and 2 interact differently with heparin-heparan sulfate" J. Biol. Chem., vol. 277, No. 32, Aug. 9, 2002, pp. 28554-28563.
Powers et al., "Fibroblast growth factors, their receptors and signaling", XP-002165147, Endocrine-Related Cancer, 7, pp. 165-197, (2000).
Rang et al, "Cancer chemotherapy," *Rang and Dale's Pharmacology*, Churchill Linvingston Elsevier, 2008, pp. 718-735.
Reis-Filho et al., "FGFR1Emerges as a PotentialTherapeuticTarget for Lobular Breast Carcinomas," 2006, Clin. Cancer Res. 12(22): 6652-6662.
Reynolds et al., "Evaluating Response to Antineoplastic Drug Combinations in Tissue Culture Models," from Methods in Molecular Medicine, vol. 110: Chemosensitivity: vol. 1: In Vitro Assays, Edited by R.D. Blumenthal, Humana Press Inc., Totowa, NJ, pp. 173-183, 2005.
Robertson et al., "Activating mutations in the extracellular domain of the fibroblast growth factor receptor 2 function by disruption of the disulfide bond in the third immunoglobulin-like domain," Proc. Natl. Acad. Sci., USA, 95: 4567-4572 (1998).
Roghani et al., "Heparin increases the affinity of basic fibroblast growth factor for its receptor but is not required for binding" J. Biol. Chem., vol. 269, No. 6, Feb. 11, 1994, pp. 3976-3984.
Ruta et al., "A novel protein tyrosine kinase gene whose expression is modulated during endothelial cell differentiation" Oncogene, 1988, vol. 3, pp. 9-15.
Sahadevan et al., Selective Over-expression of Fibroblast Growth Factor Receptors I and 4 in Clinical Prostate Cancer, Journal of Pathology, vol. 213, Jul. 2007, pp. 82-90.
Sanchez-Heras et al., "The fibroblast growth factor receptor acid box is essential for interactions with N-cadherin and all of the major isoforms of neural cell adhesion molecules," J Biol Chem, 2006, 281(46):35208-16.
Schlessinger et al., "Crystal Structure of the Ternary FGF-FGFR-Heparin Complex Reveals a Dual Role for Heparin in FGFR Binding and Dimerization," Molecular Cell, 6: 743-750 (2000).
Seshacharyulu et al., "Targeting the EGFR signaling pathway in cancer therapy," Expert Opin Ther Targets, 16(1): 15-31 (2012).
Shamim et al., "Sequential roles for Fgf4, En1 and Fgf8 in specification and regionalization of the midbrain" Development, vol. 126, Feb. 1999, pp. 945-959.
Smith et al., "The asparagine-linked oligosaccharides on tissue factor pathway inhibitor terminate with $SO_4$-4GalNAc$\beta$1,4GIcNAc$\beta$1,2Man$\alpha$" J. Biol. Chem., vol. 267, No. 27, Sep. 25, 1992, pp. 19140-19146.
St. Bernard et al., "Fibroblast growth factor receptors as molecular targets in thyroid carcinoma" Endocrinology, vol. 146, No. 3, 2005, pp. 1145-1153.
St. Bernard et al., "Fibroblast growth factor receptors as molecular targets in thyroid carcinoma" Endocrinology, vol. 10, Nov. 24, 2004, pp. 1-26 and 6 pgs. figures.
Stauber et al., "Structural interaction of fibroblast growth factor receptor with its ligands," Proc. Natl. Acad. Sci., USA, 97(1): 49-54 (2000).
Sugiura et al., "Co-expression of aFGF and FGFR-1 is predictive of a poor prognosis in patients with esophageal squamous cell carcinoma," Oncology Reports, 2007, 17: 557-564.
Tacer et al., "Research Resource: Comprehensive Expression Atlas of the Fibroblast Growth Factor System in Adult Mouse," Mol Endocrinol., 2010, 24(10):2050-2064, incl Supplemental Files, 23 pages total.
Taraboletti et al., "Potential Antagonism of Tubulin-Binding Anticancer Agents in Combination Therapies," Clin Cancer Res 11(7): 2720-2726 (2005).
Tolcher et al., "Preliminary Results of a Phase 1 Study of FP-1039 (FGFR1:Fc), A Novel Antagonist of Multiple Fibroblast Growth Factor (FGF) Ligands, In Patients With Advanced Malignancies," 2009 AACR-EORTC-NCI Molecular Targets and Cancer Therapeutics Conference Poster (Nov. 15-18, 2009).
Tolcher et al., "Preliminary Results of a Dose Escalation Study of the Fibroblast Growth Factor (FGF) "trap" FP-1039 (FGFR1:Fc) In Patients With Advanced Malignancies," 22nd EORTC-NCI-AACR Symposium on Molecular Targets and Cancer Therapeutics Poster (Nov. 16-19, 2010).
Tolcher et al., "Preliminary results of a dose escalation study of the Fibroblast Growth Factor (FGF) "trap" FP-1039 (FGFR1:Fc) in patients with advanced malignancies," *European Journal of Cancer, Supplement*, 8(7): 121, Abstract No. 381 (Nov. 18, 2010).
Tomlinson et al., "Alternative splicing of fibroblast growth factor receptor 3 produces a secreted isoform that inhibits fibroblast growth factor-induced proliferation and is repressed in urothelial carcinoma cell lines" Cancer Research, vol. 65, No. 22, Nov. 15, 2005, pp. 10441-10449.
Trueb et al., "Characterization of FGFRL1, a novel fibroblast growth factor (FGF) receptor preferentially expressed in skeletal tissues" J. Biol. Chem., vol. 278, No. 36, Sep. 5, 2003, pp. 33857-33865.
Tucker et al., "A novel approach for inhibiting growth factor signalling in murine tooth development" Eur. J. Oral Sci., vol. 106 (suppl. 1), 1998, pp. 122-125.
Tuominen et al., "Expression and glycosylation studies of human FGF Receptor 4" Protein Expression and Purification, vol. 21, Mar. 2001, pp. 275-285.
Turner et al., "FGFR1 Amplification Drives Endocrine Therapy Resistance and Is a Therapeutic Target in Breast Cancer," 2010, 70(5): 2085-2094.
Turner et al., "A Therapeutic Target for Smoking-Associated Lung Cancer," 2010, Science Trans. Med. 2(62): 62ps56, 4 pages.
Ueno et al., "A truncated form of fibroblast growth factor receptor 1 inhibits signal transduction by multiple types of fibroblast growth factor receptor" J. Biol. Chem., vol. 267, No. 3, Jan. 25, 1992, pp. 1470-1476.
Van Den Nieuwenhof et al., "Recombinant glycodelin carrying the same type of glycan structures as contraceptive glycodelin-A can be produced in human kidney 293 cells but not in Chinese hamster ovary cells" Eur. J. Biochem., vol. 267, Aug. 2000, pp. 4753-4762.
Voortman et al., "Array comparative genomic hybridization-based characterization of genetic alterations in pulmonary neuroendocrine tumors," 2010, PNAS, 107(29): 13040-13045.
Wagner et al., "Suppression of fibroblast growth factor receptor signaling inhibits pancreatic cancer growth in vitro and in vivo" Gastroenterology, vol. 114, Apr. 1998, pp. 798-807.
Wang et al., "Purification and characterization of a functional soluble fibroblast growth factor receptor 1" Biochem. Biophys. Res. Comm., vol. 203, No. 3, Sep. 30, 1994, pp. 1781-1788.
Wang et al., "A natural kinase-deficient variant of fibroblast growth factor receptor 1" Biochemistry, Vo. 35, 1996, pp. 10134-10142.
Wang et al., "Alternately Spliced NH2-terminalImmunoglobulin-like Loop I in the Ectodomain of the Fibroblast Growth Factor (FGF) Receptor 1 Lowers Affinity for both Heparin and FGF-1," J. Biol. Chem, 270(17): 10231-10235 (1995).
Weiss et al., "Frequent and Focal FGFR1 Amplification Associates with Therapeutically Tractable FGFR1 Dependency in Squamous Cell Lung Cancer," Science Trans. Med., 2010, 2(62): 62ra93, 8 pages.
Wells, "Additivity of Mutational Effects in Proteins," Biochemistry, 1990, 29(37):8509-8517.
Werner et al., "Differential splicing in the extracellular region of fibroblast growth factor receptor 1 generates receptor variants with different ligand-binding specificities" Molecular and Cellular Biology, vol. 12, No. 1, Jan. 1992, pp. 82-88.

(56) References Cited

OTHER PUBLICATIONS

Williams et al., "Activation of the FGF receptor underlies neurite outgrowth stimulated by L1, N-CAM, and N-Cadherin" Neuron, vol. 13, Sep. 1994, pp. 583-594.
Ye et al., "FGF and Shh signals control dopaminergic and serotonergic cell fate in the anterior neural plate" Cell, vol. 93, May 29, 1998, pp. 755-766.
Yoo et al., "Docetaxel Associated Pathways in Cisplatin Resistant Head and Neck Squamous Cell Carcinoma: A Pilot Study," Laryngoscope, 115: 1938-1946 (2005).
Yu et al., "Loss of fibroblast growth factor receptor 2 ligand-binding specificity in Apert syndrome," PNAS, 2000, 97(26):14536-14541.
Zhang et al., Receptor Specificity of the Fibroblast Growth Factor Family: The Complete Mammalian FGF Family, The Journal of Biological Chemistry, vol. 281, No. 23, Jun. 9, 2006, pp. 15694-15700.
Zhang et al., "FP-1039 (FGFR1:Fc), A Soluble FGFR1 Receptor Antagonist, Inhibits Tumor Growth and Angiogenesis," AACR-NCI-EORTC International Conference, Oct. 22-26, 2007, San Francisco, CA.
Zheng et al. "Enhanced efficacy in anti-tumour activity by combined therapy of recombinant FGFR-1 related angiogenesis and low-dose cytotoxic agent," European Journal of Cancer, vol. 43, No. 14, Sep. 14, 2007, pp. 2134-2139.
Zytovision GmbH, Catalogue 2011, 1st Edition, 84 pages.
File History for U.S. Appl. No. 11/791,889, filed May 30, 2007.
File History for U.S. Appl. No. 12/535,479, filed Aug. 4, 2009.
File History for U.S. Appl. No. 12/652,720, filed Jan. 5, 2010.
File History for U.S. Appl. No. 13/157,712, filed Jun. 10, 2011.
File history for U.S. Appl. No. 13/227,398, filed Sep. 7, 2011.
File History for U.S. Appl. No. 13/296,161, filed Nov. 14, 2011.
File History for U.S. Appl. No. 13/296,168, filed Nov. 14, 2011.
File History for U.S. Appl. No. 13/496,182, filed Mar. 14, 2012.
File History for U.S. Appl. No. 13/438,638, filed Apr. 3, 2012.
File History for U.S. Appl. No. 13/509,068, filed Jun. 13, 2012.
File History for U.S. Appl. No. 13/612,044, filed Sep. 12, 2012.
File History for U.S. Appl. No. 13/675,255, filed Nov. 13, 2012.
File History for U.S. Appl. No. 13/515,429, filed Nov. 21, 2012.
File History for U.S. Appl. No. 13/905,042, filed May 29, 2013.
International Search Report and Written Opinion of the International Searching Authority, mailed Sep. 18, 2007, for International Application No. PCT/US2006/028597, 23 pages.
International Preliminary Report on Patentability, mailed Jan. 22, 2008, for International Application No. PCT/US2006/028597, 14 pages.
International Search Report and written Opinion, mailed Mar. 8, 2010, for PCT/US2009/052704, filed Aug. 4, 2009.
International Search Report and Written Opinion, mailed Feb. 4, 2011, for International Patent Application PCT/US2010/056627, 15 pages.
International Search Report and Written Opinion of the International Searching Authority, mailed Jan. 31, 2012, for International Application No. PCT/US2011/060661, 16 pages.
International Search Report and Written Opinion of the International Searching Authority, mailed Apr. 12, 2012, for International Application No. PCT/US2011/060666, 20 pages.
International Search Report and Written Opinion mailed Apr. 1, 2013 for PCT/US2012/064772, 16 pages.
European Search Report, mailed Jun. 5, 2009, in European Application No. 09075061.3, 2 pages.
European Search Report, mailed May 2, 2013, in European Patent Application No. 10817774.2, 8 pages.
Invitation to Pay Additional Fees and, Where Applicable, Protest Fee, mailed Dec. 31, 2012, in international Application No. PCT/US2012/64772, 2 pages.
File History for U.S. Appl. No. 14/357,336, filed May 9, 2014.

SEQUENCE LISTING

```
<160> NUMBER OF SEQ ID NOS: 18

<210> SEQ ID NO 1
<211> LENGTH: 353
<212> TYPE: PRT
<213> ORGANISM: Homo sapiens
```

<400> SEQUENCE: 1

```
Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala Val Met Thr Ser Pro Leu Tyr Leu
            340                 345                 350

Glu
```

<210> SEQ ID NO 2
<211> LENGTH: 349
<212> TYPE: PRT
<213> ORGANISM: Homo sapiens

<400> SEQUENCE: 2

```
Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala Val Met Thr Ser Pro
            340                 345

<210> SEQ ID NO 3
<211> LENGTH: 345
<212> TYPE: PRT
<213> ORGANISM: Homo sapiens

<400> SEQUENCE: 3

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30
```

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
 50                  55                  60

Val Glu Val Gln Asp Ser Val Pro Ala Asp Ser Gly Leu Tyr Ala Cys
 65                  70                  75                  80

Val Thr Ser Ser Pro Ser Gly Ser Asp Thr Thr Tyr Phe Ser Val Asn
            85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
            115                 120                 125

Ala Pro Tyr Trp Thr Ser Pro Glu Lys Met Glu Lys Lys Leu His Ala
            130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
            165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
            195                 200                 205

Val Glu Asn Glu Tyr Gly Ser Ile Asn His Thr Tyr Gln Leu Asp Val
            210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
            245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
            275                 280                 285

Lys Thr Ala Gly Val Asn Thr Thr Asp Lys Glu Met Glu Val Leu His
            290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
            325                 330                 335

Glu Ala Leu Glu Glu Arg Pro Ala Val
            340                 345

<210> SEQ ID NO 4
<211> LENGTH: 344
<212> TYPE: PRT
<213> ORGANISM: Homo sapiens

<400> SEQUENCE: 4

Arg Pro Ser Pro Thr Leu Pro Glu Gln Ala Gln Pro Trp Gly Ala Pro
 1               5                  10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
 50                  55                  60

```
            50                  55                  60
Val Glu Val Gln Asp Ser Val Pro Ala Asp Ser Gly Leu Tyr Ala Cys
 65                  70                  75                  80

Val Thr Ser Ser Pro Ser Gly Ser Asp Thr Thr Tyr Phe Ser Val Asn
                 85                  90                  95

Val Ser Asp Ala Leu Pro Ser Ser Glu Asp Asp Asp Asp Asp Asp Asp
                100                 105                 110

Ser Ser Ser Glu Glu Lys Glu Thr Asp Asn Thr Lys Pro Asn Pro Val
                115                 120                 125

Ala Pro Tyr Trp Thr Ser Pro Glu Lys Met Glu Lys Lys Leu His Ala
            130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
                180                 185                 190

Ile Met Asp Ser Val Val Pro Ser Asp Lys Gly Asn Tyr Thr Cys Ile
            195                 200                 205

Val Glu Asn Glu Tyr Gly Ser Ile Asn His Thr Tyr Gln Leu Asp Val
            210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
                260                 265                 270

Asn Gly Ser Lys Ile Gly Pro Asp Asn Leu Pro Tyr Val Gln Ile Leu
            275                 280                 285

Lys Thr Ala Gly Val Asn Thr Thr Asp Lys Glu Met Glu Val Leu His
            290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala
            340

<210> SEQ ID NO 5
<211> LENGTH: 339
<212> TYPE: PRT
<213> ORGANISM: Homo sapiens

<400> SEQUENCE: 5

Arg Pro Ser Pro Thr Leu Pro Glu Gln Ala Gln Pro Trp Gly Ala Pro
 1               5                  10                  15

Val Glu Val Glu Ser Phe Leu Val His Pro Gly Asp Leu Leu Gln Leu
                20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
        50                  55                  60

Val Glu Val Gln Asp Ser Val Pro Ala Asp Ser Gly Leu Tyr Ala Cys
 65                 70                  75                  80
```

Val Thr Ser Ser Pro Ser Gly Ser Asp Thr Thr Tyr Phe Ser Val Asn
            85                  90                  95

Val Ser Asp Ala Leu Pro Ser Ser Glu Asp Asp Asp Asp Asp Asp Asp
           100                 105                 110

Ser Ser Ser Glu Glu Lys Glu Thr Asp Asn Thr Lys Pro Asn Pro Val
           115                 120                 125

Ala Pro Tyr Trp Thr Ser Pro Glu Lys Met Glu Lys Lys Leu His Ala
           130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
               165                 170                 175

Asp His Arg Ile Gly Gly Tyr Lys Val Arg Tyr Ala Thr Trp Ser Ile
           180                 185                 190

Ile Met Asp Ser Val Val Pro Ser Asp Lys Gly Asn Tyr Thr Cys Ile
           195                 200                 205

Val Glu Asn Glu Tyr Gly Ser Ile Asn His Thr Tyr Gln Leu Asp Val
           210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
               245                 250                 255

Tyr Ser Asp Pro Gln Pro His Ile Gln Trp Leu Lys His Ile Glu Val
           260                 265                 270

Asn Gly Ser Lys Ile Gly Pro Asp Asn Leu Pro Tyr Val Gln Ile Leu
           275                 280                 285

Lys Thr Ala Gly Val Asn Thr Thr Asp Lys Glu Met Glu Val Leu His
290                 295                 300

Leu Arg Asn Val Ser Phe Glu Asp Ala Gly Glu Tyr Thr Cys Leu Ala
               305                 310                 315                 320

Gly Asn Ser Ile Gly Leu Ser His His Ser Ala Trp Leu Thr Val Leu
               325                 330                 335

Glu Ala Leu

<210> SEQ ID NO 6
<211> LENGTH: 334
<212> TYPE: PRT
<213> ORGANISM: Homo sapiens

<400> SEQUENCE: 6

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
            85                  90                  95

Val Ser Asp Ala Leu Pro Ser Ser Glu Asp Asp Asp Asp Asp Asp Asp
           100                 105                 110

```
Ser Ser Ser Glu Glu Lys Glu Thr Asp Asn Thr Lys Pro Asn Pro Val
            115                 120                 125

Ala Pro Tyr Trp Thr Ser Pro Glu Lys Met Glu Lys Lys Leu His Ala
130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr
                325                 330

<210> SEQ ID NO 7
<211> LENGTH: 231
<212> TYPE: PRT
<213> ORGANISM: Homo sapiens

<400> SEQUENCE: 7

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160
```

```
Ile Ala Val Glu Trp Glu Ser Asn Gly Gln Pro Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 8
<211> LENGTH: 571
<212> TYPE: PRT
<213> ORGANISM: Homo sapiens

<400> SEQUENCE: 8

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
                20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
        50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
```

```
              290                 295                 300
Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
            325                 330                 335

Glu Ala Leu Glu Pro Lys Ser Ser Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 9
<211> LENGTH: 4
<212> TYPE: PRT
<213> ORGANISM: Homo sapiens

<400> SEQUENCE: 9

Leu Tyr Leu Glu
1

<210> SEQ ID NO 10
<211> LENGTH: 8
<212> TYPE: PRT
<213> ORGANISM: Homo sapiens

<400> SEQUENCE: 10

Met Thr Ser Pro Leu Tyr Leu Glu
1               5

<210> SEQ ID NO 11
<211> LENGTH: 9
<212> TYPE: PRT
```

-continued

<213> ORGANISM: Homo sapiens

<400> SEQUENCE: 11

Val Met Thr Ser Pro Leu Tyr Leu Glu
1               5

<210> SEQ ID NO 12
<211> LENGTH: 10
<212> TYPE: PRT
<213> ORGANISM: Homo sapiens

<400> SEQUENCE: 12

Ala Val Met Thr Ser Pro Leu Tyr Leu Glu
1               5                   10

<210> SEQ ID NO 13
<211> LENGTH: 14
<212> TYPE: PRT
<213> ORGANISM: Homo sapiens

<400> SEQUENCE: 13

Glu Glu Arg Pro Ala Val Met Thr Ser Pro Leu Tyr Leu Glu
1               5                   10

<210> SEQ ID NO 14
<211> LENGTH: 15
<212> TYPE: PRT
<213> ORGANISM: Homo sapiens

<400> SEQUENCE: 14

Leu Glu Glu Arg Pro Ala Val Met Thr Ser Pro Leu Tyr Leu Glu
1               5                   10                  15

<210> SEQ ID NO 15
<211> LENGTH: 16
<212> TYPE: PRT
<213> ORGANISM: Homo sapiens

<400> SEQUENCE: 15

Ala Leu Glu Glu Arg Pro Ala Val Met Thr Ser Pro Leu Tyr Leu Glu
1               5                   10                  15

<210> SEQ ID NO 16
<211> LENGTH: 17
<212> TYPE: PRT
<213> ORGANISM: Homo sapiens

<400> SEQUENCE: 16

Lys Ala Leu Glu Glu Arg Pro Ala Val Met Thr Ser Pro Leu Tyr Leu
1               5                   10                  15

Glu

<210> SEQ ID NO 17
<211> LENGTH: 21
<212> TYPE: PRT
<213> ORGANISM: Homo sapiens

<400> SEQUENCE: 17

Arg Pro Val Ala Lys Ala Leu Glu Glu Arg Pro Ala Val Met Thr Ser
1               5                   10                  15

Pro Leu Tyr Leu Glu
            20

-continued

```
<210> SEQ ID NO 18
<211> LENGTH: 17
<212> TYPE: PRT
<213> ORGANISM: Homo sapiens

<400> SEQUENCE: 18

Glu Ala Leu Glu Glu Arg Pro Ala Val Met Thr Ser Pro Leu Tyr Leu
1               5                   10                  15

Glu
```

TREATMENT OF CANCER WITH ELEVATED DOSAGES OF SOLUBLE FGFR1 FUSION PROTEINS

RELATED APPLICATIONS

This is a continuation of U.S. patent application Ser. No. 13/296,161, filed Nov. 14, 2011, now U.S. Pat. No. 8,481,038, which is a non-provisional application filed under 37 CFR 1.53(e)(1), claiming priority under 35 USC 119(e) to U.S. Provisional Application No. 61/413,940, filed Nov. 15, 2010, all of which are incorporated by reference herein in its entirety.

BACKGROUND AND SUMMARY OF THE INVENTION

The Fibroblast Growth Factor (FGF)—Fibroblast Growth Factor Receptor (FGFR) signaling pathway is widely implicated in the development and maintenance of many different cancers. This signaling pathway comprises 4 different FGF receptors (FGFR1, FGFR2, FGFR3, and FGFR4), some of which are also alternatively spliced, and 22 different FGF ligands. Each FGF receptor and splice form has different patterns of expression and different specificities for the various FGF ligands.

FGFR1 is the best characterized of the four FGFRs. FGFR1 and its ligands have causal connections to cancer in animal models and strong correlative connections to human disease. Specific induction of FGFR1 signaling in mouse prostate results in prostate hyperplasia and carcinoma (Freeman et al., *Cancer Res.* 2003; 63:8256-63), demonstrating that abnormal hyperactivation of FGFR1 is sufficient to initiate tumorigenesis. Inhibition of FGFR1 activity inhibits tumor growth in xenograft models from multiple tissue types (Ogawa et al., *Cancer Gene Ther.* 2002; 9:633-40). In human disease, chromosomal amplification of the FGFR1 gene in a subset of breast cancer patients is associated with poor outcome (Gelsi-Boyer et al., *Mol. Cancer. Res.* 2005; 3:655-67) and overexpression or high systemic levels of FGF ligands correlate with tumorigenesis and poor patient outcome (Nguyen et al., *J. Natl. Cancer Inst.* 1994; 86:356-61).

FGFR1 has multiple mechanisms in the promotion of tumor cell growth and survival. FGFR1 signaling increases the mitotic rate of tumor cells, promotes tumor angiogenesis, and helps maintain the tumorigenicity of tumor stem cells (TSCs). Many tumor cell lines are responsive to and dependent on FGFR1 signaling for growth in vitro, and tumor cell lines become resistant to cytotoxic agents when stimulated with FGF-2 (Song et al., *PNAS* 2000; 97:8658-63). Disruption of the FGF-FGFR1 pathway leads to reduction of tumor cell growth in vitro and in xenografts (Ogawa et al., *Cancer Gene Titer.* 2002; 9:633-40). Specific inhibition of FGFR signaling may therefore cause reduction in the growth rate of human tumors.

Some FGFs have potent angiogenic activities and play important roles in tumor vasculogenesis (Compagni et al., *Cancer Res.* 2000; 60:7163-69). In murine models of pancreatic cancer, FGFs mediate escape from anti-vascular endothelial growth factor receptor (VEGFR) therapy. A similar phenomenon is seen in glioblastoma multiforme patients treated with anti-VEGFR therapy, in whom tumor progression correlates with greatly increased levels of FGF-2 (Batchelor et al., *Cancer Cell* 2006; 11:83-95). Inhibition of FGFR1 might reduce tumor angiogenesis, particularly in tumors previously treated with anti-VEGF therapies.

There is increasing evidence that tumors contain a small population of malignant cells (TSCs) that are phenotypically similar to stem cells that may be responsible for tumor initiation, survival, proliferation, and recurrence. These cells are dependent on the presence of FGFs to maintain their TSC phenotypes (Dvorak et al., *FEBS Letters* 2006; 580:2869-74). When FGFs are withdrawn from in vitro cultures of TSCs, they stop proliferating and appear to differentiate. Thus, inhibition of FGFR1 signaling may lead to reduced metastases and recurrence of tumors.

Soluble FGFR1 fusion proteins are able to bind to FGF ligands of the FGFR1 receptor, "trapping" the ligands and prevent them from activating FGFR1 receptors as well as other receptors for which the ligands have affinity. See, e.g., U.S. Pat. No. 7,678,890. Without being bound to a particular theory, it is believed that soluble FGFR 1 fusion proteins can inhibit tumorigenic activity through multiple mechanisms of action, including but not limited to, direct anti-tumor activity in cancers dependent on the FGF-FGFR pathway, inhibition of tumor angiogenesis, and/or inhibition of cancer stem cell maintenance.

The data provided here show for the first time that a soluble FGFR1/Fc fusion protein, FP-1039, can be administered safely to human patients at concentrations of about 2 mg/kg body weight or higher (i.e., up to at least about 16 mg/kg) and that such concentrations are well-tolerated. As shown in detail in the Examples, in some embodiments, treatment of humans with FP-1039 yields pharmacokinetic and pharmacodynamic profiles that indicate weekly or less frequent administration of doses above 2 mg/kg, 4 mg/kg, 8 mg/kg or 10 mg/kg is sufficient for sustained sequestration of target FGF ligands such as FGF-2.

In one aspect, the present invention provides methods of treating a human having a cancer. In some embodiments, the method comprises administering to the human a therapeutically effective amount of a soluble Fibroblast Growth Factor Receptor 1 (FGFR1) fusion protein, wherein the fusion protein comprises an extracellular domain of an FGFR1 polypeptide linked to a fusion partner. In some embodiments, FGFR1 fusion protein is administered at a dose of about 2, 4, 6, 8, 10, 12, 14, 16, 18, 20, 22, 24, 25, 26, 28 or 30 mg/kg body weight, or within a range from one to another of the above dose values (the above doses being calculated using an extinction coefficient of 1.42 mL/mg*cm). In some embodiments, the FGFR1 fusion protein is administered at a dose of about 10 mg/kg body weight as calculated using an extinction coefficient of 1.11 mL/mg*cm. In other embodiments, the FGFR1 fusion protein is administered at a dose of about 20 mg/kg body weight as calculated using an extinction coefficient of 1.11 mL/mg*cm, or at a range of about 10 to about 20 mg/kg body weight as calculated using an extinction coefficient of 1.11 mL/mg*cm. In some embodiments, the human has a fibroblast growth factor-2 (FGF-2) plasma concentration of at least 6 pg/ml. In some embodiments, the cancer is characterized by a ligand-dependent activating mutation in FGFR2. In some embodiments, the ligand-dependent activating mutation in FGFR2 is S252W or P253R. In some embodiments, the soluble FGFR1 fusion protein is administered in combination with a chemotherapeutic agent or a VEGF antagonist.

In some embodiments, the FGFR1 polypeptide is human FGFR1 isoform IIIc. In some embodiments, the fusion partner is an Fc polypeptide, which is the Fc region of human immunoglobulin G1 (IgG1). In some embodiments, the FGFR1 extracellular domain has the amino acid sequence of SEQ ID NO:5. In some embodiments, the soluble FGFR1 fusion protein has the amino acid sequence of SEQ ID NO:8.

In some embodiments, the soluble FGFR1 fusion protein is administered at a dose of about 2 mg/kg body weight to about 30 mg/kg body weight. In some embodiments, the soluble FGFR1 fusion protein is administered at a dose of about 8 mg/kg body weight to about 16 mg/kg body weight (or about 10 mg/kg body weight to about 20 mg/kg body weight when calculated using an extinction coefficient of 1.11 mL/mg*cm). In some embodiments, the soluble FGFR1 fusion protein is administered at a dose of about 8 mg/kg body weight, while in some embodiments, the soluble FGFR1 fusion protein is administered at a dose of about 16 mg/kg body weight (or at about 10 mg/kg body weight or about 20 mg/kg body weight, respectively, when calculated using an extinction coefficient of 1.11 mL/mg*cm).

In some embodiments, the method comprises administering FP-1039 to a human patient having cancer, wherein the human has a fibroblast growth factor-2 (FGF-2) plasma concentration of at least 6 pg/ml and wherein FP-1039 is administered at a dose of about 2 mg/kg to about 30 mg/kg. In some embodiments, the soluble FGFR1 fusion protein is administered at a dose of about 8 mg/kg body weight. In some embodiments, the FP-1039 is administered at about 16 mg/kg.

In some embodiments, the soluble FGFR1 fusion protein is administered twice a week, weekly, every other week, at a frequency between weekly and every other week, every three weeks, every four weeks, or every month.

In some embodiments, the soluble FGFR1 fusion protein is administered intravenously or subcutaneously.

In some embodiments, the cancer is prostate cancer, breast cancer, colorectal cancer, lung cancer, endometrial cancer, head and neck cancer, laryngeal cancer, liver cancer, renal cancer, glioblastoma, or pancreatic cancer.

In some embodiments, the human has an FGF-2 plasma concentration of at least 10 pg/ml prior to the administration of the soluble FGFR1 fusion protein. In some embodiments, the soluble FGFR1 fusion protein is administered at a dose such that at seven days after administration, the human has an FGF-2 plasma concentration of less than 4 pg/ml.

In some embodiments, the soluble FGFR1 fusion protein is administered in combination with a chemotherapeutic agent. In some embodiments, the chemotherapeutic agent is sorafenib. In some embodiments, the soluble FGFR1 fusion protein is administered in combination with a VEGF antagonist. In some embodiments, the VEGF antagonist is a VEGF antibody, such as bevacizumab, or the VEGF antagonist is a VEGF trap, such as aflibercept. In some embodiments, the soluble FGFR1 fusion protein is administered in combination with an anti-angiogenic agent.

The present invention also provides for methods of treating a human having a cancer, wherein the cancer is characterized by an Fibroblast Growth Factor Receptor 2 (FGFR2) having a ligand-dependent activating mutation, the method comprising: administering to the human a soluble Fibroblast Growth Factor Receptor 1 (FGFR1) fusion protein at a dose of about 2 mg/kg body weight to about 30 mg/kg body weight, wherein the fusion protein comprises an extracellular domain of an FGFR1 polypeptide linked to a Fc polypeptide. In some embodiments, the soluble FGFR1 fusion protein is administered at a dose of about 8 mg/kg body weight, while in some embodiments, the FP-1039 is administered at about 16 mg/kg body weight (or about 10 mg/kg body weight or about 20 mg/kg body weight, respectively when calculated using an extinction coefficient of 1.11 mL/mg*cm).

In some embodiments wherein the cancer is characterized by an FGFR2 having a ligand-dependent activating mutation, the FGFR1 polypeptide is human FGFR1 isoform IIIc. In some embodiments wherein the cancer is characterized by an FGFR2 having a ligand-dependent activating mutation, the Fc polypeptide is an Fc region of human immunoglobulin G1 (IgG1).

In some embodiments for treating cancer characterized by an FGFR2 having a ligand-dependent activating mutation, the FGFR 1 extracellular domain comprises the amino acid sequence of SEQ ID NO:5. In some embodiments, the soluble FGFR1 fusion protein comprises the amino acid sequence of SEQ ID NO:8.

In some embodiments for treating cancer characterized by an FGFR2 having a ligand-dependent activating mutation, the soluble FGFR1 fusion protein is administered at a dose of about 2 mg/kg body weight to about 30 mg/kg body weight. In some embodiments for treating cancer characterized by an FGFR2 having a ligand-dependent activating mutation, the soluble FGFR1 fusion protein is administered at a dose of about 8 mg/kg body weight to about 16 mg/kg body weight (or about 10 mg/kg body weight to about 20 mg/kg body weight when calculated using an extinction coefficient of 1.11 mL/mg*cm). In some embodiments for treating cancer characterized by an FGFR2 having a ligand-dependent activating mutation, the soluble FGFR1 fusion protein is administered at a dose of about 8 mg/kg body weight, while in some embodiments for treating cancer characterized by an FGFR2 having a ligand-dependent activating mutation, the soluble FGFR1 fusion protein is administered at a dose of about 16 mg/kg body weight (or about 10 mg/kg body weight or about 20 mg/kg body weight, respectively when calculated using an extinction coefficient of 1.11 mL/mg*cm). In some embodiments for treating cancer characterized by an FGFR2 having a ligand-dependent activating mutation, the FGFR1 fusion protein is administered at a dose of about 2, 4, 6, 8, 10, 12, 14, 16, 18, 20, 22, 24, 25, 26, 28 or 30 mg/kg body weight, or within a range from one to another of the above dose values. In some embodiments, dosages may be administered weekly, every other week, at a frequency between weekly and every other week, every three weeks, every four weeks, or every month.

In some embodiments for treating cancer characterized by an FGFR2 having a ligand-dependent activating mutation, the method comprises administering FP-1039 to a human patient having cancer, wherein the cancer is characterized by an FGFR2 having a ligand-dependent activating mutation, and wherein FP-1039 is administered at a dose of about 2 mg/kg to about 30 mg/kg. In some embodiments, the FP-1039 is administered at about 8 mg/kg, while in some embodiments, the FP-1039 is administered at about 16 mg/kg (or about 10 mg/kg body weight to about 20 mg/kg body weight when calculated using an extinction coefficient of 1.11 mL/mg*cm).

In some embodiments for treating cancer characterized by an FGFR2 having a ligand-dependent activating mutation, the soluble FGFR1 fusion protein is administered weekly or every other week or a frequency between weekly and every other week.

In some embodiments for treating cancer characterized by an FGFR2 having a ligand-dependent activating mutation, the soluble FGFR1 fusion protein is administered intravenously or subcutaneously.

In some embodiments for treating cancer characterized by an FGFR2 having a ligand-dependent activating mutation, the cancer is prostate cancer, breast cancer, colorectal cancer, lung cancer, endometrial cancer, head and neck cancer, laryngeal cancer, liver cancer, renal cancer, glioblastoma, or pancreatic cancer.

In some embodiments for treating cancer characterized by an FGFR2 having a ligand-dependent activating mutation, the human has an FGF-2 plasma concentration of at least 10 pg/ml prior to the administration of the soluble FGFR1 fusion protein. In some embodiments for treating cancer characterized by an FGFR2 having a ligand-dependent activating mutation, the soluble FGFR1 fusion protein is administered at a dose such that at seven days after administration, the human has an FGF-2 plasma concentration of less than 4 pg/ml.

In some embodiments for treating cancer characterized by an FGFR2 having a ligand-dependent activating mutation, the soluble FGFR1 fusion protein is administered in combination with a chemotherapeutic agent. In some embodiments, the chemotherapeutic agent is sorafenib. In some embodiments for treating cancer characterized by an FGFR2 having a ligand-dependent activating mutation, the soluble FGFR1 fusion protein is administered in combination with a chemotherapeutic agent, VEGF antagonist or anti-angiogenic agent. In some embodiments, the VEGF antagonist is a VEGF antibody, such as bevacizumab, or the VEGF antagonist is a VEGF trap, such as aflibercept. In some embodiments, the soluble FGFR1 fusion protein is administered in combination with an anti-angiogenic agent.

In some embodiments for treating cancer characterized by an FGFR2 having a ligand-dependent activating mutation, the ligand-dependent activating mutation in FGFR2 is S252W or P253R.

The present invention also provides a composition comprising a soluble FGFR1 fusion protein for use in the treatment of cancer, wherein the composition is administered at a dose of at least about 2, 4, 6, 8, 10, 12, 14, 16, 18, 20, 22, 24, 25, 26, 28 or 30 mg/kg body weight, or within a range from one to another of the above dose values. In some embodiments, dosages may be administered twice a week, weekly, every other week, at a frequency between weekly and every other week, every three weeks, every four weeks, or every month. In some embodiments, the human has a fibroblast growth factor-2 (FGF-2) plasma concentration of at least 6 pg/ml. In some embodiments, the cancer is characterized by a ligand-dependent activating mutation in FGFR2. In some embodiments, the ligand-dependent activating mutation in FGFR2 is S252W or P253R. In some embodiments, the soluble FGFR1 fusion protein is administered in combination with a chemotherapeutic agent or a VEGF antagonist.

Any embodiment described herein or any combination thereof applies to any and all methods of the invention described herein.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only.

As used herein, all numbers are approximate, and may be varied to account for measurement error and the rounding of significant digits. The use of "about" before certain measured quantities includes variations due to sample impurities, measurement error, human error, and statistical variation, as well as the rounding of significant digits.

As used herein, a "fibroblast growth factor receptor 1" or "FGFR1" polypeptide refers to a polypeptide having the amino acid sequence of any one of the known FGFR 1 polypeptides, such as FGFR1-IIIb and FGFR1-IIIc, and any variant, precursor, or fragment thereof, including those described in U.S. Pat. Nos. 7,678,890; 6,656,728; 6,384,191; 6,255,454; 6,344,546; 5,288,855; and 5,229,501. An FGFR1 polypeptide sequence is typically from, or derived from, a mammal including, but not limited to, primate, e.g., human; rodent, e.g., rat, mouse, hamster; cow; pig; sheep; horse; or any other mammal.

As used herein, "extracellular domain" or "ECD" refers to the portion of a polypeptide that extends beyond the transmembrane domain of the polypeptide into the extracellular space. In some embodiments, the ECD is an ECD of an FGFR1 polypeptide, such as FGFR1-IIIb and FGFR1-IIIc, or a variant thereof. The term "FGFR1 extracellular domain" ("FGFR1 ECD") includes full-length FGFR1 ECDs, FGFR1 ECD fragments, and FGFR1 ECD variants. As used herein, the term "FGFR1 ECD" refers to an FGFR1 polypeptide that lacks the intracellular and transmembrane domains, with or without a signal peptide. In some embodiments, the FGFR1 ECD comprises an amino acid sequence that is substantially identical to an ECD having the amino acid sequence of SEQ ID NO:1. In some embodiments, the FGFR1 ECD has the amino acid sequence of any of SEQ ID NOs:1-6.

As used herein, a "soluble FGFR fusion protein" or an "FGFR1 fusion protein" or "FGFR1 ECD fusion molecule" refers to a protein comprising an FGFR1 ECD linked to one or more fusion partners, wherein the soluble FGFR fusion protein lacks a transmembrane domain (e.g., an FGFR1 transmembrane domain) and is not bound to the cellular membrane.

As used herein, a "fusion partner" is a molecule that is linked to the FGFR1 ECD that imparts favorable pharmacokinetics and/or pharmacodynamics on the FGFR1 ECD protein. A fusion partner may comprise a polypeptide, such as a fragment of an immunoglobulin molecule or albumin, or it may comprise a non-polypeptide moiety, for example, polyethylene glycol. In some embodiments, the fusion partner is an Fc domain of an antibody.

The term "signal peptide" refers to a sequence of amino acid residues located at the N terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Exemplary signal peptides also include signal peptides from heterologous proteins. A "signal sequence" refers to a polynucleotide sequence that encodes a signal peptide. In some embodiments, an FGFR1 ECD lacks a signal peptide. In some embodiments, an FGFR1 ECD includes at least one signal peptide, which may be a native FGFR1 signal peptide or a heterologous signal peptide.

A "ligand-dependent activating mutation" of FGFR2 refers to a mutation that increases the biological activity of FGFR2, for example, a mutation causing FGFR2 to become activated more readily in comparison to the wildtype FGFR2 in response to certain stimuli, wherein the biological effects of the mutation depend on the binding of FGFR2 to one or more of its ligands. An example is a mutation that causes alterations in the ligand binding properties of FGFR2.

As used herein, the terms "native FGFR1 ECD" and "wildtype FGFR1 ECD" are used interchangeably to refer to an FGFR1 ECD with a naturally occurring amino acid sequence. Native FGFR1 ECDs and wildtype FGFR1 ECDs also include FGFR1 ECD splice variants or isoforms. As used herein, the terms FGFR1 ECD "splice variants" or "splice isoforms" are used interchangeably to refer to alternative splice forms of FGFR1 ECD, such as FGFR1-IIIb and FGFR1-IIIc ECD.

As used herein, the term "FGFR1 ECD variants" refers to FGFR1 ECDs containing amino acid additions, deletions, and/or substitutions in comparison to the native FGFR1 ECDs. FGFR1 ECD variants retain the ability to bind FGF2. Such variants may be at least 90%, 92%, 95%, 97%, 98%, or 99% identical to the parent FGFR1 ECD.

The term "full-length FGFR1 ECD", as used herein, refers to an FGFR1 ECD that extends to the last amino acid of the extracellular domain, and may or may not include an N-terminal signal peptide. As used herein, the term "FGFR1 ECD fragment" refers to an FGFR1 ECD having an amino acid sequence modified in that amino acid residues have been deleted from the amino-terminus and/or from the carboxy-terminus of the polypeptide, wherein the fragment retains the ability to bind FGF2. As used herein, the term "native FGFR1 ECD fragment" refers to an FGFR1 ECD fragment in which the retained portions of the FGFR1 ECD sequence are naturally occurring, wherein the fragment retains the ability to bind FGF2.

As used herein, the terms "FGFR1 ECD fragment variant" and "variant of FGFR1 ECD fragment" are used interchangeably to refer to FGFR1 ECDs containing, not only amino acid deletions from the amino- and/or carboxy-terminus of native FGFR1 ECD, but also amino acid additions, deletions, and/or substitutions within the retained portion of the FGFR1 ECD. FGFR1 ECD fragment variants also retain the ability to bind FGF2.

The terms "nucleic acid" or "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "peptide," "polypeptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The terms also include post-translational modifications of the polypeptide, including, for example, glycosylation, sialylation, acetylation, and phosphorylation. When a polypeptide "consists of" a particular amino acid sequence, it may still contain post-translational modifications, such as glycosylation and sialylation.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, $\gamma$-carboxyglutamate, and O-phosphoserine. Amino acid analogs refer to compounds that have the same basic chemical structure as a naturally occurring amino acid, i.e., a $\gamma$-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and 8) Cysteine (C), Methionine (M) (see, e.g., Creighton, *Proteins* (1984))

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The invention provides polypeptides that are substantially identical to the polypeptides exemplified herein (e.g., the polypeptides exemplified in SEQ ID NOs:1-8). Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, $M=5$, $N=-4$, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two polypeptides are substantially identical is that the first polypeptide is immunologically cross reactive with the antibodies raised against the second polypeptide. Thus, a polypeptide is typically substantially identical to a second polypeptide, for example, where the two peptides differ only by conservative substitutions.

The terms "cancer" and "cancerous" refer to or describe the physiological condition in mammals that is typically characterized by unregulated cell growth. In some embodiments, cancer is a human cancer. Examples of cancer include but are not limited to carcinomas, sarcomas, adenocarcinomas, lymphomas, leukemias, solid and lymphoid cancers, etc. Examples of different types of cancer include, but are not limited to, pancreatic cancer, breast cancer, gastric cancer, bladder cancer, oral cancer, ovarian cancer, thyroid cancer, lung cancer (non-small cell lung cancer, small cell lung cancer, squamous cell lung cancer), (non-small cell lung cancer, small cell lung cancer, squamous cell lung cancer), prostate cancer, uterine cancer, endometrial cancer, testicular cancer, neuroblastoma, squamous cell carcinoma of the head, neck, cervix and vagina, multiple myeloma, soft tissue and osteogenic sarcoma, colorectal cancer, liver cancer (i.e., hepatocarcinoma), renal cancer (i.e., renal cell carcinoma), mesothelioma, cervical cancer, anal cancer, bile duct cancer, gastrointestinal carcinoid tumors, gastrointestinal stromal tumors (GIST), esophageal cancer, laryngeal cancer, gall bladder cancer, small intestine cancer, cancer of the central nervous system, skin cancer, choriocarcinoma; osteogenic sarcoma, rhabdomyosarcoma, fibrosarcoma, glioma, glioblastoma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, and acute myelocytic leukemia. Cancers embraced in the current application include both metastatic and non-metastatic cancers.

The terms "treating" or "treatment" refers to inhibiting a disease, i.e., arresting or reducing the development of the disease or its clinical symptoms; or relieving a disease, for example, by causing regression, or restoring or repairing a lost, missing, or defective function; or stimulating an inefficient process. In some embodiments, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

The terms "subject" and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets. In some embodiments, the subject is a human.

A "pharmaceutically acceptable carrier" refers to a solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. Pharmaceutically acceptable carriers are determined in part by the particular composition being administered, as well as by the particular method used to administer the composition.

"FP-1039" refers to a protein having the amino acid sequence set forth in SEQ ID NO:8. FP-1039 can be produced, for example, as is described generally for FGFR fusion molecules in U.S. Pat. No. 7,678,890, the entire disclosure of which is expressly incorporated herein by reference.

The term "anti-neoplastic composition" refers to a composition useful in treating cancer comprising at least one active therapeutic agent, e.g., "anti-cancer agent." Examples of therapeutic agents (anti-cancer agents) include, but are not limited to, e.g., chemotherapeutic agents, growth inhibitory agents, cytotoxic agents, agents used in radiation therapy, anti-angiogenic agents, apoptotic agents, anti-tubulin agents, and other-agents to treat cancer, such as anti-VEGF antibodies (e.g., bevacizumab, AVASTIN®), anti-HER-2 antibodies (e.g., trastuzumab, HERCEPTIN®), anti-CD20 antibodies (e.g., rituximab, RITUXAN®), an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., *Angew. Chem. Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), pemetrexed (ALIMTA®); tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib, NEXAVAR®; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestins such as megestrol acetate and medroxyprogesterone acetate, estrogens such as diethylstilbestrol and premarin, and androgens/retinoids such as fluoxymesterone, all transretinoic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

An "angiogenic factor or agent" is a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family (VEGF-B, VEGF-C and VEGF-D), PlGF, PDGF family, fibroblast growth factor family (FGFs), TIE ligands (Angiopoietins), ephrins, delta-like ligand 4 (DLL4), del-1, fibroblast growth factors: acidic (aFGF) and basic (bFGF), follistatin, granulocyte colony-stimulating factor (G-CSF), hepatocyte growth factor (HGF)/scatter factor (SF), interleukin-8 (IL-8), leptin, midkine, neuropilins, placental growth factor (PlGF), platelet-derived endothelial cell growth factor (PD-ECGF), platelet-derived growth factor, especially PDGF-BB or PDGFR-beta, Pleiotrophin (PTN), progranulin, proliferin, transforming growth factor-alpha (TGF-alpha), transforming growth factor-beta (TGF-beta), tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenic agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenic agent includes those agents that bind and block the angiogenic activity of the angiogenic factor or its receptor. For example, an anti-angiogenic agent is an antibody or other antagonist to an angiogenic agent as defined above, e.g., fusion proteins that binds to VEGF-A such as ZALTRAP™ (Aflibercept), antibodies to VEGF-A such as AVASTIN® (bevacizumab) or to the VEGF-A receptor (e.g., KDR receptor or Flt-1 receptor), anti-PDGFR inhibitors such as GLEEVEC® (Imatinib Mesylate), small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogenic agents also include native angiogenesis inhibitors, e.g., angiostatin, endostatin, etc. See, e.g., Klagsbrun and D'Amore (1991) Annu. Rev. Physiol. 53:217-39; Streit and Detmar (2003) Oncogene 22:3172-3179 (e.g., Table 3 listing anti-angiogenic therapy in malignant melanoma); Ferrara & Alitalo (1999) Nature Medicine 5(12):1359-1364; Tonini et al. (2003) Oncogene 22:6549-6556 (e.g., Table 2 listing known anti-angiogenic factors); and, Sato (2003) Int. J. Clin. dOncol. 8:200-206 (e.g., Table 1 listing anti-angiogenic agents used in clinical trials).

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) Science 246:1306, and Houck et al. (1991) Mol. Endocrin, 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)," "VEGF-A$_{109}$" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

A "VEGF antagonist" refers to a molecule capable of neutralizing, blocking, abrogating, reducing or interfering with VEGF activities including, but not limited to, its binding to one or more VEGF receptors. VEGF antagonists include, without limitation, anti-VEGF antibodies and antigen-binding fragments thereof, receptor molecules and derivatives which bind specifically to VEGF thereby sequestering its binding to one or more receptors, anti-VEGF receptor antibodies, VEGF receptor antagonists such as small molecule inhibitors of the VEGFR tyrosine kinases, and immunoadhesins that bind to VEGF such as VEGF traps (e.g., aflibercept). The term "VEGF antagonist," as used herein, specifically includes molecules, including antibodies, antibody fragments, other binding polypeptides, peptides, and non-peptide small molecules, that bind to VEGF and are capable of neutralizing, blocking, inhibiting, abrogating, reducing or interfering with VEGF activities. Thus, the term "VEGF activities" specifically includes VEGF mediated biological activities of VEGF.

The term "VEGF trap" as used herein means a protein, such as a fusion molecule, that binds to VEGF and is capable of neutralizing, blocking, inhibiting, abrogating, reducing or interfering with VEGF activities. An example of a VEGF trap is aflibercept.

The term "anti-VEGF antibody" or "an antibody that binds to VEGF" refers to an antibody that is capable of binding to VEGF with sufficient affinity and specificity that the antibody is useful as a diagnostic and/or therapeutic agent in targeting VEGF. Anti-VEGF antibodies suppress the growth of a variety of human tumor cell lines in nude mice (Kim et al., Nature 362:841-844 (1993); Warren et al., J. Clin. Invest. 95:1789-1797 (1995); Borgström et al., Cancer Res. 56:4032-4039 (1996); Melnyk et al., Cancer Res. 56:921-924 (1996)) and also inhibit intraocular angiogenesis in models of ischemic retinal disorders. Adamis et al., Arch. Ophlhalmol. 114:66-71 (1996). For example, the anti-VEGF antibody can be used as a therapeutic agent in targeting and interfering with diseases or conditions wherein the VEGF activity is involved. See, e.g., U.S. Pat. Nos. 6,582,959, 6,703,020; WO98/45332; WO 96/30046; WO94/10202, WO2005/044853; EP 0666868B1; US Patent Applications 20030206899, 20030190317, 20030203409, 20050112126, 20050186208, and 20050112126; Popkov et al., Journal of Immunological Methods 288:149-164 (2004); and WO2005012359. The antibody selected will normally have a sufficiently strong binding affinity for VEGF. For example, the antibody may bind hVEGF with a $K_d$ value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. The antibody may be subjected to other biological activity assays, e.g., in order to evaluate its effectiveness as a therapeutic. Such assays are known in the art and depend on the target antigen and intended use for the antibody. Examples include the HU VEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B, VEGF-C, VEGF-D or VEGF-E, nor other growth factors such as PlGF, PDGF or bFGF.

In one embodiment, anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody (see Presta et al. (1997) Cancer Res. 57:4593-4599), including but not limited to the antibody known as "bevacizumab" also known as "rhuMAb VEGF" or "AVASTIN®." AVASTIN® is presently commercially available. Nonlimiting exemplary cancers that may be treated with bevacizumab include non-small cell lung cancer, colorectal cancer, breast cancer, renal cancer, ovarian cancer, glioblastoma multiforme, pediatric osteosarcoma, gastric cancer and pancreatic cancer. Bevacizumab comprises mutated human IgG$_1$ framework regions and antigen-binding complementarity-determining regions from the murine antibody A.4.6.1 that blocks binding of human VEGF to its receptors. Bevacizumab and other humanized anti-VEGF antibodies are further described in U.S. Pat. Nos. 6,884,879, and 7,169,901.

Additional anti-VEGF antibodies are described in PCT Application Publication Nos. WO2005/012359 and WO2009/073160; U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004).

A "effective amount" or "therapeutically effective amount" refers to an amount of a drug effective to treat a disease or disorder in a subject. In certain embodiments, an effective amount refers to an amount effective, at dosages and for periods of time necessary, to achieve the desired therapeutic or prophylactic result. A therapeutically effective amount of FGFR1 fusion protein of the invention may vary according to factors such as the disease state, age, sex, and weight of the individual, and the ability of the substance/molecule, agonist or antagonist to elicit a desired response in the individual. A therapeutically effective amount is also one in which any toxic or detrimental effects of the FGFR1 fusion proteins are outweighed by the therapeutically beneficial effects. In the case of cancer, the effective amount of the drug may reduce the number of cancer cells; reduce the tumor size; inhibit (i.e., slow to some extent and typically stop) cancer cell infiltration into peripheral organs; inhibit (i.e., slow to some extent and typically stop) tumor metastasis; inhibit, to some extent, tumor growth; allow for treatment of the tumor, and/or relieve to some extent one or more of the symptoms associated with the disorder. To the extent the drug may prevent growth and/or kill existing cancer cells, it may be cytostatic and/or cytotoxic.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Herein, "concurrent" dosing refers to the administration of two therapeutic molecules within an eight hour time period. In some embodiments, two therapeutic molecules are administered at the same time. Two therapeutic molecules are considered to be administered at the same time (i.e. simultaneously) if at least a portion of a dose of each therapeutic molecule is administered within 1 hour. Two therapeutic molecules are administered concurrently if at least one dose is administered concurrently, even if one or more other doses are not administered concurrently. In some embodiments, concurrent administration includes a dosing regimen when the administration of one or more therapeutic molecule(s) continues after discontinuing the administration of one or more other therapeutic molecules(s).

Administration "in combination with" one or more further therapeutic agents includes concurrent (including simultaneous) and consecutive (i.e., sequential) administration in any order.

DETAILED DESCRIPTION OF THE INVENTION

I. Introduction

Figure 1:
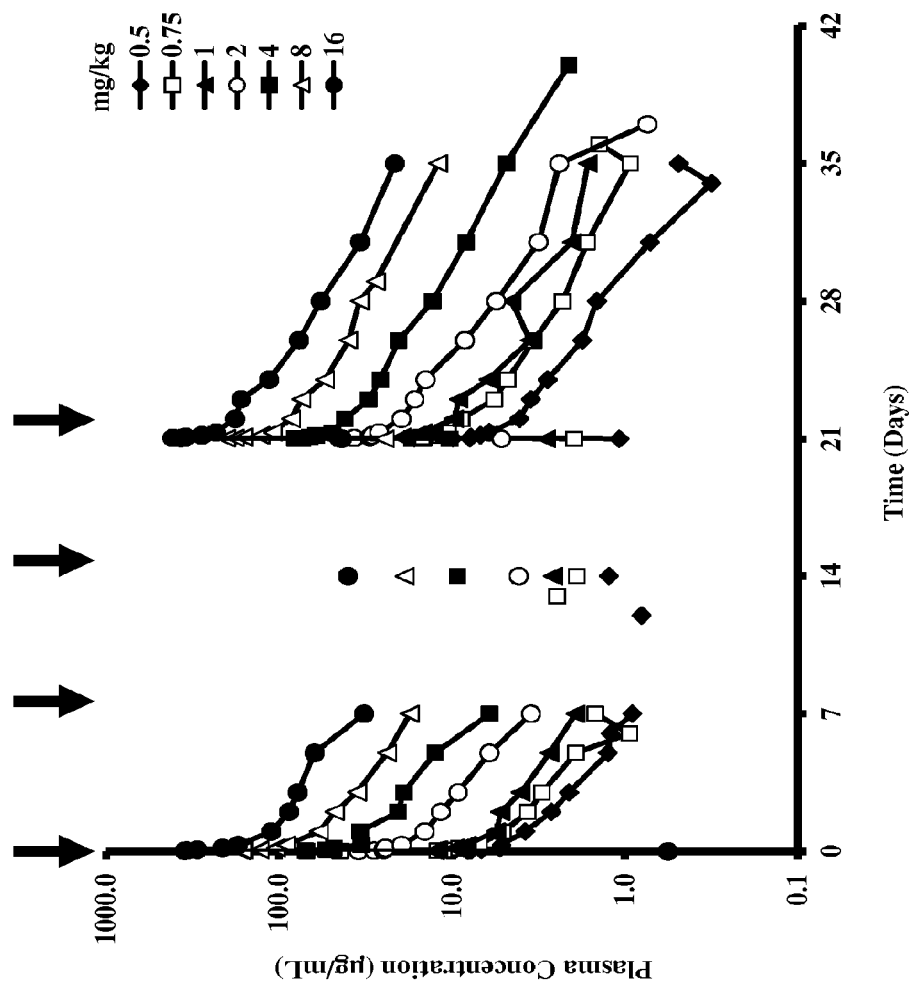
FIG. 1. Pharmacokinetics of FP-1039 at doses from 0.5-16.0 mg/kg. Arrows indicate days of FP-1039 administration. PK samples on Days 8 and 15 are pre-dose (trough), while detailed PK sampling is performed following Dose 1 (Day 1) and after 4 weekly doses (Day 22).

The data provided here show for the first time that a soluble Fibroblast Growth Factor Receptor 1 (FGFR1)/Fc fusion protein, FP-1039, can be administered safely to human patients at concentrations at about 0.5 mg/kg body weight (i.e., up to at least about 16 mg/kg) and that such concentrations are well-tolerated. Accordingly, the present invention provides for administration of FP-1039 (i.e., SEQ ID NO:8) to human individuals, e.g., cancer patients, at concentrations from a dose of about 2 mg/kg body weight to at least about 30 mg/kg. In view of these new data, it is believed that other soluble FGFR1 fusion proteins can also be safely administered to humans at these same elevated concentrations, for example, to treat cancer.

II. Methods of Treatment

The present invention provides methods of treating a human having a cancer, the method comprising administering to the human a soluble FGFR1 fusion protein (e.g., FP-1039) as described herein at a dose of about 2 mg/kg body weight to about 30 mg/kg body weight.

In some embodiments, the human having a cancer has an FGF-2 plasma concentration above the average FGF-2 plasma concentration of the human without cancer. In some embodiments, the human having a cancer has an FGF-2 plasma concentration of at least 6 pg/ml or at least 10 pg/ml prior to the administration of the soluble FGFR1 fusion protein. In some embodiments, as used herein, FGF-2 levels are determined as measured by an electrochemiluminescence (ECL) assay (Meso Scale Discovery, Gaithersburg, Md.), which utilizes an anti-FGF-2 antibody (Meso Scale Discovery) as the primary antibody and a ruthenium metal chelate (Sulfo-Tag) anti-human growth factor antibody blend as the secondary antibody. Detection is accomplished using a reader such as MSD SI2400 reader (Meso Scale Discovery, Sector Image 2400, Model #1250). For detecting FGF-2 levels, the manufacturer's instructions are followed, with the following modification: the Assay Diluent GF1 is replaced with Calibrator Diluent GF1.

In another aspect, the method of treating the human having the cancer comprises administering soluble FGFR1 fusion protein (e.g., FP-1039) in a dose that results in sustained target engagement in the plasma even after seven days post-administration or longer. In some embodiments, the soluble FGFR1 fusion protein is administered in a dose that results in sustained engagement of the target FGF-2 in the plasma even after seven days post-administration or longer. Thus, in some embodiments, the soluble FGFR1 fusion protein is administered at a dose such that, at seven days after administration, the human has a free FGF-2 plasma concentration of less than 4 pg/ml. In some embodiments, the soluble FGFR1 fusion protein is administered at a dose such that, at seven days after administration, the human has a free FGF-2 plasma concentration of less than 3 pg/ml. In some embodiments as described in this paragraph, the soluble FGFR1 fusion protein consists of or comprises SEQ ID NO:8.

A. Conditions Suitable for Treatment

The soluble FGFR1 fusion proteins of the present invention (including but not limited to FP-1039) find use in treating both metastatic and non-metastatic forms of cancer, including but not limited to, pancreatic cancer, breast cancer, gastric cancer, bladder cancer, oral cancer, ovarian cancer, thyroid cancer, lung cancer, prostate cancer, uterine cancer, endometrial cancer, testicular cancer, neuroblastoma, squamous cell carcinoma of the head, neck, cervix and vagina, multiple myeloma, soft tissue and osteogenic sarcoma, colorectal cancer, liver cancer (i.e., hepatocarcinoma), renal cancer (i.e., renal cell carcinoma), mesothelioma, cervical cancer, anal cancer, bile duct cancer, gastrointestinal carcinoid tumors, gastrointestinal stromal tumors (GIST), esophageal cancer, laryngeal cancer, gall bladder cancer, small intestine cancer, cancer of the central nervous system, skin cancer, choriocarcinoma; osteogenic sarcoma, rhabdomyosarcoma, fibrosarcoma, glioma, glioblastoma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, and acute myelocytic leukemia. In some embodiments, the cancer to be treated is prostate cancer, breast cancer, colorectal cancer, lung cancer, endometrial cancer, head and neck cancer, laryngeal cancer, liver cancer, renal cancer, glioblastoma or pancreatic cancer.

In some embodiments, the humans treated with a soluble FGFR1 fusion protein have a cancer that is characterized by a Fibroblast Growth Factor Receptor 2 (FGFR2) with a ligand-dependent activating mutation. A ligand-dependent activating mutant is a FGFR2 variant whose biological effects depend on the binding of FGFR2 to one or more of its ligands, such as a mutation that causes alterations in the ligand binding properties of FGFR2. An observed FGFR2 mutation in endometrial tumor cells is S252W, found in about 7% of cases. In addition, a P253R mutation occurs in about 2% of endometrial cancer cases. These S252W and P253R mutations are the same mutations found in the germline of patients with the genetic disease Apert Syndrome, which causes craniosynostosis and syndactyl). Structural and biochemical studies of the FGFR2 S252W mutant receptor suggest that S252W and P253R mutants may cause the FGFR2 protein to bind more tightly to its normal FGF ligands as well as to bind other FGF ligands to which it normally does not bind. See K. Yu et al., *Proc. Natl. Acad. Sci. USA* 97: 14536-41 (2000); O. A. Ibrahimi et al., *Proc. Natl. Acad. Sci. USA* 98: 7182-87 (2001).

In some embodiments, expression of an FGFR2 having a ligand-dependent activating mutation is detected by biopsying the cancer and analyzing the nucleic acid of the tumor cells of the cancer. Whether the ligand-dependent activating mutation is detectably expressed in the nucleic acid can be analyzed using any method known in the art, including but not limited to polymerase chain reaction (PCR), quantitative PCR, RT-PCR, or sequencing analysis. In some embodiments, expression of an FGFR2 having a ligand-dependent activating mutation is detected in tumor cells by PCR amplification and sequencing of exon 7 of the genomic FGFR2 gene using primer sequences described by Dutt et al., *PNAS* 105(25):8713-7 (2008).

B. Dosages, Formulations and Duration

The compositions of the present invention will be formulated, dosed, and administered in a fashion consistent with good medical practice. Factors for consideration in this context include, but are not limited to, the particular disorder being treated, the particular mammal being treated, the clinical condition of the individual patient, the cause of the disorder, the site of delivery of the agent, the method of administration, the scheduling of administration, and other factors known to medical practitioners. For the prevention or treatment of disease, the appropriate dosage of an FGFR1 fusion protein of the invention (when used alone or in combination with one or more other additional therapeutic agents) will depend on the type of disease to be treated, the severity and course of the disease, whether the FGFR1 fusion protein is administered for preventive or therapeutic purposes, the intended aggressiveness of the treatment regime, previous therapy, the patient's clinical history and response to the FGFR1 fusion protein, and the discretion of the attending physician.

The compositions for administration will commonly comprise a soluble FGFR1 fusion protein (i.e., an extracellular domain of an FGFR1 polypeptide linked to a Fc polypeptide, such as but not limited to FP-1039) dissolved in a pharmaceutically acceptable carrier, e.g., an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of soluble FGFR1 fusion protein in these formulations can vary widely, and will be selected primarily based on fluid volumes, viscosities, body weight and the like in accordance with the particular mode of administration selected and the patient's needs.

Thus, a typical pharmaceutical composition for administration will vary according to the agent and method of administration (e.g. intravenous or subcutaneous). Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

Pharmaceutical formulations for use with the present invention can be prepared by mixing a soluble FGFR1 fusion protein having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidant (e.g., ascorbic acid); preservatives; low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g., Zn-protein complexes); and/or non-ionic surfactants.

In some embodiments, the soluble FGFR1 fusion protein (including but not limited to FP-1039) is administered at a dose of about 2 mg/kg body weight to about 30 mg/kg body weight. In some embodiments, the soluble FGFR1 fusion protein (including but not limited to FP-1039) is administered at a dose of about 8 mg/kg body weight to about 20 mg/kg body weight. In some embodiments, the soluble FGFR1 fusion protein (including but not limited to FP-1039) is administered at a dose of about 8 mg/kg body weight, about 10 mg/kg body weight, about 11 mg/kg body weight, about 12 mg/kg body weight, about 13 mg/kg body weight, about 14 mg/kg body weight, about 15 mg/kg body weight, about 16 mg/kg body weight, about 17 mg/kg body weight, about 18 mg/kg body weight, about 19 mg/kg body weight, about 20 mg/kg body weight, about 24 mg/kg body weight, or about 30 mg/kg body weight, or in a dose ranging from one to another of the above values. In some embodiments, dosages may be administered twice a week, weekly, every other week, at a frequency between weekly and every other week, every three weeks, every four weeks, or every month.

In certain embodiments, dosages of the soluble FGFR1 fusion protein can be calculated in two ways depending on the extinction coefficient (EC) used. The extinction coefficient differs depending on whether the glycosylation of the protein is taken into account. In one embodiment, the extinction coefficient based on the amino acid composition of FP-1039, for example, is 1.42 mL/mg*cm. In another embodiment, when the carbohydrate portion as well as the protein portion of FP-1039 is accounted for, the extinction coefficient is 1.11 mL/mg*cm. Calculation of the FP-1039 dose using an EC of 1.11 mL/mg*cm increases the calculated dose by 28%, as shown in Table 1. Although the doses calculated using the two extinction coefficients are different, the molar concentrations, or the actual amounts of drug administered, are identical. Unless otherwise noted, the doses disclosed herein are each calculated using the extinction coefficient that does not take account of glycosylation. For FP-1039, this extinction coefficient is 1.42 mL/mg*cm. How these dosages compare to those calculated using the extinction coefficient that takes account of glycosylation is shown in Table 1. As can be seen from Table 1, a dosage of 8 mg/kg (e.g., 7.8 and 8.0) using an EC of 1.42 mL/mg*cm herein corresponds to a dosage of 10 mg/kg (e.g. 10.0 and 10.2) when calculated using an EC of 1.11 mL/mg*cm. A dosage of 16 mg/kg (e.g. 15.6 and 16.0 mg/kg) herein using an EC of 1.42 mL/mg*cm corresponds to a dosage of about 20 mg/kg (e.g. 20.0 and 20.5) when calculated using an EC of 1.11 mL/mg*cm. As noted in the "Definitions" section above, measured numbers provided herein are approximate and encompass values having additional significant digits that are rounded off. For instance, 8 mg/kg encompasses values with two significant digits such as 7.6, 7.8, 8.0, 8.2, 8.4, and 8.45, each of which round to 8. Likewise, a value such as 16 mg/kg encompasses values with three significant digits that round to 16, such as, for example 15.6 and 16.0.

TABLE 1

Conversion of FP-1039 Dose

| Dose$^a$ EC = 1.42 mL/mg * cm | Dose$^a$ EC = 1.11 mL/mg * cm |
|---|---|
| 0.5 | 0.6 |
| 0.75 | 1.0 |
| 1.0 | 1.3 |
| 2.0 | 2.6 |
| 3.0 | 3.8 |
| 4.0 | 5.1 |
| 5.0 | 6.4 |
| 6.0 | 7.7 |
| 7.0 | 9.0 |
| 7.8 | 10.0 |
| 8.0 | 10.2 |
| 9.0 | 11.5 |
| 10.0 | 12.8 |
| 11.0 | 14.1 |
| 12.0 | 15.4 |
| 13.0 | 16.6 |
| 14.0 | 17.9 |
| 15.0 | 19.2 |
| 15.6 | 20.0 |
| 16.0 | 20.5 |
| 17.0 | 21.8 |
| 18.0 | 23.0 |
| 19.0 | 24.3 |
| 20.0 | 25.6 |
| 30.0 | 38.4 |

$^a$Doses shown in mg/kg.

In some embodiments, the patient is treated with a combination of the FGFR1 fusion protein (e.g., FP-1039) and one or more other therapeutic agents(s). The combined administration includes coadministration or concurrent administration, using separate formulations or a single pharmaceutical formulation, and consecutive administration in either order, wherein optionally there is a time period while both (or all) active agents simultaneously exert their biological activities. The effective amounts of therapeutic agents administered in combination with an FGFR1 fusion protein will be at the physician's or veterinarian's discretion. Dosage administration and adjustment is done to achieve maximal management of the conditions to be treated. The dose will additionally depend on such factors as the type of therapeutic agent to be used and the specific patient being treated.

In some embodiments, the patient is treated with a combination of the FGFR1 fusion protein (e.g., FP-1039) and a VEGF antagonist. In some embodiments, the VEGF antagonist is a VEGF trap, such as aflibercept. In some embodiments, the VEGF antagonist is a VEGF antibody. In some embodiments, the VEGF antibody is bevacizumab. One exemplary dosage of bevacizumab would be in the range from about 0.05 mg/kg to about 20 mg/kg. Thus, one or more doses of about 0.5 mg/kg, 2.0 mg/kg, 4.0 mg/kg, 7.5 mg/kg, 10 mg/kg or 15 mg/kg (or any combination thereof) may be administered to the patient. Such doses may be administered intermittently, e.g., every week, every two, or every three weeks.

In some embodiments, the FGFR1 fusion protein (e.g., FP-1039) is administered in combination with another therapeutic agent, such as chemotherapeutic agent or anti-angiogenic agent, at the recommended or prescribed dosage and/or frequency of the therapeutic agent.

C. Methods of Administration

The soluble FGFR1 fusion proteins of the present invention are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The administration may be local or systemic. In some embodiments, the soluble FGFR1 fusion proteins are administered intravenously. The methods described herein are based on administering a soluble FGFR1 fusion protein to a human patient as a continuous infusion over a period of 30 minutes. However, the present invention also contemplates administering the soluble FGFR1 fusion protein over a shorter or longer period of time, e.g., over a period of one hour.

The compositions comprising the FGFR1 fusion proteins of the invention can be administered as needed to subjects. In certain embodiments, an effective dose of the FGFR1 fusion proteins of the invention is administered to a subject one or more times. In various embodiments, an effective dose of the FGFR1 fusion proteins of the invention is administered to the subject at least once a month, at least twice a month, once a week, twice a week, or three times a week. In various embodiments, an effective dose of the FGFR1 fusion proteins of the invention is administered to the subject for at least a week, at least a month, at least three months, at least six months, or at least a year.

D. Combination Therapy

The FGFR1 fusion proteins of the present invention may be administered alone or with other modes of treatment. They may be provided before, substantially contemporaneous with, or after other modes of treatment, for example, surgery, chemotherapy, radiation therapy, or the administration of other therapeutics, including for example, small molecules and other biologics, such as a therapeutic antibody.

In some embodiments, an FGFR1 fusion protein of the present invention is the only therapeutically active agent administered to a patient. In certain embodiments, the FGFR1 fusion protein is administered in combination with one or more other therapeutic agents, including but not limited to anti-angiogenic agents, chemotherapeutic agents, cytokines, growth inhibitory agents, anti-hormonal agents, kinase inhibitors, cytotoxic agents, cardioprotectants, or other therapeutic agents. The FGFR1 fusion protein may be administered concurrently with one or more other therapeutic regimens. In some embodiments, the FGFR1 fusion protein may be administered in combination with one or more antibodies.

Anti-angiogenic therapy in relationship to cancer is a cancer treatment strategy aimed at inhibiting the development of tumor blood vessels required for providing nutrients to support tumor growth. In some embodiments, because angiogenesis is involved in both primary tumor growth and metastasis, the anti-angiogenic treatment provided by the invention is capable of inhibiting the neoplastic growth of tumor at the primary site as well as preventing metastasis of tumors at the secondary sites, therefore allowing attack of the tumors by other therapeutics. In one embodiment of the invention, anti-cancer agent or therapeutic is an anti-angiogenic agent. In another embodiment, anti-cancer agent is a chemotherapeutic agent.

Many anti-angiogenic agents have been identified and are known in the arts, including those listed herein, e.g., listed under Definitions, and by, e.g., Carmeliet and Jain, *Nature* 407:249-257 (2000); Ferrara et al., *Nature Reviews: Drug Discovery*, 3:391-400 (2004); and Sato *Int. J. Clin. Oncol.*, 8:200-206 (2003). See also, US Patent Application US20030055006. In some embodiments, two or more angiogenic inhibitors may optionally be co-administered to the patient in addition to an FGFR1 fusion protein of the invention.

In some embodiments, other therapeutic agents that may be combined with the FGFR1 fusion protein are VEGF antagonists or VEGF receptor antagonists. In some embodiments, other therapeutic agents useful for combination tumor therapy with the FGFR1 fusion protein include antagonists of other factors that are involved in tumor growth, such as EGFR, ErbB2 (also known as Her2) ErbB3, ErbB4, or TNF. In some embodiments, the FGFR1 fusion protein can be used in combination with small molecule receptor tyrosine kinase inhibitors (RTKIs) that target one or more tyrosine kinase receptors such as VEGF receptors, FGF receptors, EGF receptors and PDGF receptors. Many therapeutic small molecule RTKIs are known in the art, including, but are not limited to, vatalanib (PTK787), erlotinib (TARCEVA®), OSI-7904, ZD6474 (ZACTIMA®), ZD6126 (ANG453), ZD1839, sunitinib (SUTENT®), semaxanib (SU5416), AMG706, AG013736, Imatinib (GLEEVEC®), MLN-518, CEP-701, PKC-412, Lapatinib (GSK572016), VELCADE®, AZD2171, sorafenib (NEXAVAR®), XL880, and CHIR-265.

In some embodiments, the FGFR1 fusion protein and the one or more other therapeutic agents can be administered concurrently, simultaneously, or sequentially in an amount and for a time sufficient to reduce or eliminate the occurrence or recurrence of a tumor, a dormant tumor, or a micrometastases. The FGFR1 fusion protein and the one or more other therapeutic agents can be administered as maintenance therapy to prevent or reduce the likelihood of recurrence of the tumor.

III. Soluble FGFR1 Fusion Proteins

A. FGFR1 ECD Fusion Molecules

Soluble FGFR1 fusion proteins or FGFR1 ECD fusion molecules, refer to proteins comprising an FGFR1 ECD polypeptide linked to at least one fusion partner, wherein the soluble FGFR1 fusion protein lacks a transmembrane domain (e.g., an FGFR1 transmembrane domain) and is not bound to the cellular membrane. The fusion partner may be joined to either the N-terminus or the C-terminus of the FGFR1 ECD polypeptide. When the fusion partner is a polypeptide, the FGFR1 ECD may be joined to either the N-terminus or the C-terminus of the fusion partner.

B. FGFR1 ECDs

FGFR1 ECD molecules are provided. In some embodiments, FGFR1 ECDs consist of native FGFR1 ECDs, FGFR1 ECD variants, FGFR1 ECDs comprising an Ig domain III chosen from IIIb and IIIc, native FGFR1-IIIb ECD, native FGFR1-IIIc ECD, FGFR1-IIIb ECD variants, FGFR1-IIIc ECD variants, FGFR1 ECD fragments, native FGFR1 ECD fragments, variants of FGFR1 ECD fragments, FGFR1 ECD glycosylation mutants, and FGFR1 ECD fusion molecules, as well as non-human FGFR1 ECDs. All FGFR1 ECDs are able to bind FGF-2. In some embodiments, the FGFR1 ECD includes a signal peptide, either from FGFR1, or from another FGFR, or from another protein. In other embodiments, no signal peptide is included.

The FGFR1 ECD proteins of the invention can comprise an entire FGFR ECD, including that of wildtype FGFR1-IIIb or wildtype FGFR1-IIIc ECD, or for example a variant or fragment of the FGFR1 ECD (e.g., a variant or fragment having at least 95% amino acid sequence identity to a wildtype FGFR1 ECD) that retains the ability to bind FGF-2. In some embodiments, a variant of the native FGFR1 ECD, for example, lacking the first immunoglobulin domain is provided. See, e.g., U.S. Pat. No. 6,384,191. In some embodiments, a variant of the native FGFR1 ECD having a deletion of one or more and up to 22 amino acid residues counting from the C-terminus of the native FGFR1 ECD of SEQ ID NO:1, is provided. In some embodiments, the FGFR1 ECD has the final 22 amino acids of the C-terminus deleted, while in others, the FGFR1 ECD has the final 19, 14, 9, 8, or 4 C-terminal amino acids deleted in comparison to SEQ ID NO:1. See, e.g., SEQ ID NOs:2-6.

In some embodiments, the FGFR1 ECD of the present invention has at least 90%, at least 92%, at least 95%, at least 96%, at least 97%, at least 98%, at least 99%, or higher amino acid sequence identity to a wildtype FGFR1-IIIc ECD (SEQ ID NO:1). In some embodiments, the FGFR1 ECD of the present invention has at least 90%, at least 92%, at least 95%, at least 96%, at least 97%, at least 98%, at least 99%, or higher amino acid sequence identity to a wildtype FGFR1-IIIc ECD (SEQ ID NO:1) and has the ability to bind FGF-2.

Non-limiting exemplary FGFR1 ECD fragments include human FGFR1 ECD ending at amino acid 339 (counting from the first amino acid of the mature form, without the signal peptide). In some embodiments, an FGFR1 ECD fragment ends at an amino acid between amino acid 339 and amino acid 360 (counting from the first amino acid of the mature form, without the signal peptide).

Examples of FGFR1 ECD fragments include those having the C-terminal amino acid residues LYLE (SEQ ID NO:9) or MTSPLYLE (SEQ ID NO:10) or VMTSPLYLE (SEQ ID NO:11) or AVMTSPLYLE (SEQ ID NO:12) or EERPAVMTSPLYLE (SEQ ID NO:13) or LEERPAVMTSPLYLE (SEQ ID NO:14) or ALEERPAVMTSPLYLE (SEQ ID NO:15) deleted as compared to either a native FGFR1-IIIb or FGFR1-IIIc. Further examples include those having the C-terminal amino acid residues KALEERPAVMTSPLYLE (SEQ ID NO:16) or RPVAKALEERPAVMTSPLYLE (SEQ ID NO:17) deleted as compared to a native FGFR1-IIIb or EALEERPAVMTSPLYLE (SEQ ID NO:18) deleted as compared to a native FGFR1-IIIc. Point mutations, truncations, or internal deletions or insertions within the ECD amino acid sequence may be made within the FGFR1 ECD so long as FGF-2 binding activity is retained.

C. Fusion Partners and Conjugates

In certain embodiments, a fusion partner is selected that imparts favorable pharmacokinetics and/or pharmacodynamics on the FGFR1 ECD protein. For example, in certain embodiments, a fusion partner is selected that increases the half-life of the FGFR1 ECD fusion molecule relative to the corresponding FGFR1 ECD without the fusion partner. By increasing the half-life of the molecule, a lower dose and/or less-frequent dosing regimen may be required in therapeutic treatment. Further, the resulting decreased fluctuation in FGFR1 ECD serum levels may improve the safety and tolerability of the FGFR1 ECD-based therapeutics.

Many different types of fusion partners are known in the art. One skilled in the art can select a suitable fusion partner according to the intended use. Non-limiting exemplary fusion partners include polymers, polypeptides, lipophilic moieties, and succinyl groups. Exemplary polypeptide fusion partners include serum albumin (e.g. human serum albumin or HSA) and an antibody Fc domain. Exemplary polymer fusion partners include, but are not limited to, polyethylene glycol, including polyethylene glycols having branched and/or linear chains.

D. Oligomerization Domain Fusion Partners

In various embodiments, oligomerization offers certain functional advantages to a fusion protein, including, but not limited to, multivalency, increased binding strength, and the combined function of different domains. Accordingly, in certain embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains, and certain immunoglobulin domains. Certain exemplary coiled-coil polypeptide fusion partners include the tetranectin coiled-coil domain; the coiled-coil domain of cartilage oligomeric matrix protein; angiopoietin coiled-coil domains; and leucine zipper domains. Certain exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

E. Antibody Fc Immunoglobulin Domain Fusion Partners

Many Fc domains that could be used as fusion partners are known in the art. One skilled in the art can select an appropriate Fc domain fusion partner according to the intended use. In certain embodiments, a fusion partner is an Fc immunoglobulin domain. An Fc fusion partner may be a wildtype Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. In some embodiments, the Fc fusion partner does not include an Fc hinge region. Certain additional Fc fusion partners include, but are not limited to, human IgA and IgM. In certain embodiments, an Fc fusion partner comprises a C237S mutation. In certain embodiments, an Fc fusion partner comprises a hinge, CH2, and CH3 domains of human IgG2 with a P331S mutation, as described in U.S. Pat. No. 6,900,292.

F. Albumin Fusion Partners and Albumin-Binding Molecule Fusion Partners

In certain embodiments, a fusion partner is an albumin. Certain exemplary albumins include, but are not limited to, human serum albumin (HSA) and fragments of HSA that are capable of increasing the serum half-life and/or bioavailability of the polypeptide to which they are fused. In certain embodiments, a fusion partner is an albumin-binding molecule, such as, for example, a peptide that binds albumin or a molecule that conjugates with a lipid or other molecule that binds albumin. In certain embodiments, a fusion molecule comprising HSA is prepared as described, e.g., in U.S. Pat. No. 6,686,179.

G. Polymer Fusion Partners

In certain embodiments, a fusion partner is a polymer, for example, polyethylene glycol (PEG). PEG may comprise branched and/or linear chains. In certain embodiments, a fusion partner comprises a chemically-derivatized polypeptide having at least one PEG moiety attached. Pegylation of a polypeptide may be carried out by any method known in the art. One skilled in the art can select an appropriate method of pegylating a particular polypeptide, taking into consideration the intended use of the polypeptide. Certain exemplary PEG attachment methods include, for example, EP 0 401 384; Malik et al., *Exp. Hematol.*, 20:1028-1035 (1992); Francis, *Focus on Growth Factors*, 3:4-10 (1992); EP 0 154 316; EP 0 401 384; WO 92/16221; and WO 95/34326. As non-limiting examples, pegylation may be performed via an acylation reaction or an alkylation reaction, resulting in attachment of one or more PEG moieties via acyl or alkyl groups. In certain embodiments, PEG moieties are attached to a polypeptide through the α- or ε-amino group of one or more amino acids, although any other points of attachment known in the art are also contemplated.

Pegylation by acylation typically involves reacting an activated ester derivative of a PEG moiety with a polypeptide. A non-limiting exemplary activated PEG ester is PEG esterified to N-hydroxysuccinimide (NHS). As used herein, acylation is contemplated to include, without limitation, the following types of linkages between a polypeptide and PEG: amide, carbamate, and urethane. See, e.g., Chamow, *Bioconjugate Chem.*, 5:133-140 (1994). Pegylation by alkylation typically involves reacting a terminal aldehyde derivative of a PEG moiety with a polypeptide in the presence of a reducing agent. Non-limiting exemplary reactive PEG aldehydes include PEG propionaldehyde, which is water stable, and mono C1-C10 alkoxy or aryloxy derivatives thereof. See, e.g., U.S. Pat. No. 5,252,714.

In certain embodiments, a pegylation reaction results in poly-pegylated polypeptides. In certain embodiments, a pegylation reaction results in mono-, di-, and/or tri-pegylated polypeptides. Further, desired pegylated species may be separated from a mixture containing other pegylated species and/or unreacted starting materials using various purification techniques known in the art, including among others, dialysis, salting-out, ultrafiltration, ion-exchange chromatography, gel filtration chromatography, and electrophoresis.

H. Exemplary Attachment of Fusion Partners

The fusion partner may be attached, either covalently or non-covalently, to the amino-terminus or the carboxy-terminus of the FGFR1 ECD. The attachment may also occur at a location within the FGFR1 ECD other than the amino-terminus or the carboxy-terminus, for example, through an amino acid side chain (such as, for example, the side chain of cysteine, lysine, histidine, serine, or threonine).

In either covalent or non-covalent attachment embodiments, a linker may be included between the fusion partner and the FGFR1 ECD. Such linkers may be comprised of amino acids and/or chemical moieties. Exemplary methods of covalently attaching a fusion partner to an FGFR1 ECD include, but are not limited to, translation of the fusion partner and the FGFR1 ECD as a single amino acid sequence and chemical attachment of the fusion partner to the FGFR1 ECD. When the fusion partner and the FGFR1 ECD are translated as single amino acid sequence, additional amino acids may be included between the fusion partner and the FGFR1 ECD as a linker. In certain embodiments, the linker is selected based on the polynucleotide sequence that encodes it, to facilitate cloning the fusion partner and/or FGFR1 ECD into a single expression construct (for example, a polynucleotide containing a particular restriction site may be placed between the polynucleotide encoding the fusion partner and the polynucleotide encoding the FGFR1 ECD, wherein the polynucleotide containing the restriction site encodes a short amino acid linker sequence).

When the fusion partner and the FGFR1 ECD are covalently coupled by chemical means, linkers of various sizes can typically be included during the coupling reaction. Several methods of covalent coupling of a polypeptide to another molecule (i.e. fusion partner) are known. The polypeptide and fusion partner can also be non-covalently coupled. Exemplary methods of non-covalently attaching a fusion partner to an FGFR1 ECD include, but are not limited to, attachment through a binding pair. Exemplary binding pairs include, but are not limited to, biotin and avidin or streptavidin, an antibody and its antigen, etc.

I. Polynucleotides Encoding FGFR1 Fusion Proteins

Nucleic acid molecules encoding FGFR1 ECDs and/or soluble FGFR1 fusion proteins can be synthesized by chemical methods or prepared by techniques well known in the art. See, for example, Sambrook, et al., *Molecular Cloning, A Laboratory Manual*, Vols. 1-3, Cold Spring Harbor Press, Cold Spring Harbor, N.Y. (1989).

In some embodiments, a polynucleotide encoding a polypeptide of the invention comprises a nucleotide sequence that encodes a signal peptide, which, when translated, will be fused to the amino-terminus of the FGFR1 polypeptide. In other embodiments, the nucleotide sequence does not include a sequence encoding a signal peptide. As discussed above, the signal peptide may be the native signal peptide, the signal peptide of FGFR1, FGFR2, FGFR3, or FGFR4, or may be another heterologous signal peptide. Exemplary signal peptides are known in the art, and are described, e.g., in PCT Publication No. WO 2006/081430.

In some embodiments, the nucleic acid molecule comprising the polynucleotide encoding the soluble FGFR1 fusion protein is an expression vector that is suitable for expression in a selected host cell. In some embodiments, the polynucleotide encoding the FGFR1 ECD polypeptide (e.g., the polynucleotide encoding the polypeptide of any of SEQ ID NOs: 1-6) is inserted into the expression vector at a linker site, and the polynucleotide encoding the fusion partner polypeptide (e.g., the polynucleotide encoding the Fc polypeptide of human IgG1) is inserted at a site following the FGFR1 ECD such that the FGFR1 ECD and Fc components are in-frame when the nucleic acid molecule is transcribed and translated.

J. Production and Purification of FGFR1 Fusion Proteins

Cell lines and methods of producing soluble FGFR1 fusion proteins are described in U.S. Pat. No. 7,678,890.

The FGFR1 fusion proteins of the present invention may be expressed from a vector in a host cell. In some embodiments, a vector is selected that is optimized for expression of polypeptides in CHO-S or CHO-S-derived cells. Exemplary such vectors are described, e.g., in Running Deer et al., *Biotechnol. Prog.* 20:880-889 (2004). In some embodiments, a vector is chosen for in vivo expression of the polypeptides of the invention in animals, including humans. In some embodiments, expression of the polypeptide is under the control of a promoter that functions in a tissue-specific manner.

Suitable host cells for expression of the FGFR1 fusion proteins of the present invention include, for example, prokaryotic cells, such as bacterial cells; or eukaryotic cells, such as fungal cells, plant cells, insect cells, and mammalian cells. Exemplary eukaryotic cells that can be used to express polypeptides include, but are not limited to, Cos cells, including Cos 7 cells; 293 cells, including 293-6E and 293-T cells; CHO cells, including CHO-S and DG44 cells; and NS0 cells.

Introduction of a nucleic acid vector into a desired host cell can be accomplished by any method known in the art, including, but not limited to, calcium phosphate transfection, DEAE-dextran mediated transfection, cationic lipid-mediated transfection, electroporation, transduction, infection, etc. Certain exemplary methods are described, e.g., in Sambrook et al., *Molecular Cloning, A Laboratory Manual*, $3^{rd}$ ed. Cold Spring Harbor Laboratory Press (2001). Nucleic acids may be transiently or stably transfected in the desired host cells, according to methods known in the art.

In some embodiments, a polypeptide can be produced in vivo in an animal that has been engineered or transfected with a nucleic acid molecule encoding the polypeptide, according to methods known in the art.

The FGFR1 fusion proteins of the present invention can be purified by various methods known in the art. Such methods include, but are not limited to, the use of affinity matrices, ion exchange chromatography, and/or hydrophobic interaction chromatography. Suitable affinity ligands include any ligands of the FGFR1 ECD or of the fusion partner, or antibodies thereto. For example, in the case of a fusion protein, a Protein A, Protein G, Protein A/G, or an antibody affinity column may be used to bind to an Fc fusion partner to purify a polypeptide of the invention. Antibodies to the polypeptides of the invention may also be used to purify the polypeptides of the invention. Hydrophobic interactive chromatography, for example, a butyl or phenyl column, may also suitable for purifying certain polypeptides. Many methods of purifying polypeptides are known in the art Methods of constructing DNA coding sequences, vectors, and host cells for FGFR1 ECDs, as well as methods of expressing and purifying FGFR1 ECDs are also described, for example, in WO2007/014123 and in U.S. patent application Ser. No. 12/535,479 and PCT Application PCT/US09/52704, each filed Aug. 4, 2009.

EXAMPLES

The following examples are offered to illustrate, but not to limit the claimed invention. It is understood that various other embodiments may be practiced, given the general description provided above.

Example 1

Dose-Finding Study to Evaluate the Safety and Tolerability of the FGFR1-Fc Fusion Protein FP-1039 in Patients with Advanced Malignancies FP-1039 (SEQ ID NO:8) is a highly glycosylated, dimerized, soluble fusion protein consisting of a truncated extracellular domain of human FGFR1 linked to the Fc region of human IgG$_1$. In preclinical studies, FP-1039 demonstrated significant anti-tumor activity in a variety of different xenograft models; enhanced anti-tumor activity when combined with cytotoxic or targeted anti-cancer drugs; and inhibited both FGF- and VEGF-mediated angiogenesis.

A Phase I clinical trial with FP-1039 had dosing cohorts at 0.5 mg/kg body weight through 16 mg/kg body weight. Inclusion criteria included subjects having histologically or cytologically proven metastatic or locally advanced, unresectable solid tumors for which standard curative or palliative measures do not exist or are no longer effective; Eastern Cooperative Oncology Group (ECOG) Performance Status grade 0-2 (see Oken et al., *Am. J. Clin. Oncol.* 5:649-655 (1982), incorporated by reference herein in its entirety); and washout of prior anti-cancer therapy.

FP-1039 was administered to subjects intravenously over 30 minutes once a week for 4 infusions, followed by a two-week observation period. Based on the observation of two dose-limiting toxicities (DLTs) in the three subjects dosed at 1 mg/kg (one episode of bowel perforation and sepsis and one episode of grade 3 neutropenia), doses of 0.5 mg/kg and 0.75 mg/kg were explored. Six subjects were dosed at 0.5 mg/kg and six subjects were dosed at 0.75 mg/kg. As shown in Table 3 below, adverse effects included one adverse effect was observed at 0.5 mg/kg (grade 1 erythema) and one adverse effect was observed at 0.75 mg/kg (grade 2 urticaria). Other adverse events were observed but were not responsible for removal of subjects from treatment due to the adverse effects.

Although protocol-defined DLTs were observed in patients at 1 mg/kg and 0.75 mg/kg doses, dose-escalation was continued beyond 1 mg/kg, and cohorts of subjects were tested at FP-1039 dose levels of 2.0 mg/kg, 4.0 mg/kg, 8.0 mg/kg, and 16.0 mg/kg. In total, 33 subjects have been dosed to date (including those subjects dosed as described above). The tumor types for the subjects enrolled in the clinical trial are shown in Table 2.

TABLE 2

Cohorts and Dispositions of Subjects Treated

| Tumor Type | Number of Subjects (n = 33) |
| --- | --- |
| Prostate cancer | 5 |
| Breast cancer | 7 |
| [a]Sarcoma | 6 |
| [b]Hepatobiliary | 2 |
| [c]Colorectal cancer | 4 |
| Lung cancer | 3 |

TABLE 2-continued

Cohorts and Dispositions of Subjects Treated

| Tumor Type | Number of Subjects (n = 33) |
| --- | --- |
| Endometrial cancer | 1 |
| Laryngeal cancer | 1 |
| [d]Carcinoma of salivary gland | 2 |
| Carcinoid | 1 |
| Pancreatic cancer | 1 |

[a]Combines: liposarcoma, sarcoma of leg, leiomyosarcoma, chondrosarcoma, and mixed Mullerian Duct sarcoma
[b]Combines: hepatocellular carcinoma and cholangiosarcoma
[c]Combines: adenocarcinoma of colon and rectal carcinoma and adenocarcinoma of small bowel
[d]Combines: cancer of salivary gland and adenoid cystic carcinoma Safety For each cohort, FP-1039 was administered intravenously over 30 minutes once a week for 4 infusions, followed by a two-week observation period. Safety of the dosing level was evaluated by assessing for adverse events at each visit. Adverse Events were graded by the Common Terminology Criteria for Adverse Events v3.0 (CTCAE). DLT was defined as any FP-1039-associated Adverse Event of CTCAE grade 3 or higher. After completion of the initial treatment and observation period, subjects with no evidence of disease progression or DLT after 4 infusions were eligible to receive additional weekly infusions of FP-1039. The cohorts of subjects and dispositions or best responses for each cohort are shown in Table 3.

TABLE 3

Cohorts and Dispositions of Subjects Treated

| Original FP-1039 Dose Level (mg/kg) | Number of Subjects | Disposition/Best Response[a] |
| --- | --- | --- |
| 16.0 | 4 | 3 SD, 1 PD |
| 8.0 | 5 | 4 PD, 1 SD, |
| 4.0 | 3 | 3 SD |
| 2.0 | 3 | 3 PD |
| 1.0 | 6 | 2 SD, 3 PD, 1 SAE[b] |
| 0.75 | 6 | 2 SD, 1 AE[d], 3 PD |
| 0.5 | 6 | 3 SD, 1 AE[c], 2 PD |

AE: Adverse Event;
PD: Progressive Disease;
SAE: Serious Adverse Event;
SD: Stable Disease
[a]Column indicates best response or if subjects withdrew from treatment due to AEs
[b]Bowel perforation and sepsis in patient with tumor in bowel wall
[c]Grade 1 erythema
[d]Grade 2 urticaria in patient with history of allergies Generally, FP-1039 was well-tolerated without observations of drug-related weight loss, hypertension, or soft tissue calcification at doses up through 16 mg/kg. No DLTs were observed in the 15 subjects dosed from 2 mg/kg to 16 mg/kg.

Pharmacokinetics

The pharmacokinetics of FP1-1039 dosing cohorts (0.5 mg/kg, 0.75 mg/kg, 1 mg/kg, 2 mg/kg, 4 mg/kg, and 8 mg/kg) was analyzed at multiple timepoints. Plasma samples were drawn at various times after the first infusion, on Days 8, 15, and 22 immediately following dosing, and at various times following dosing on Day 22. For sample collection generally, whole blood was collected in K$_2$EDTA tubes, processed into plasma, aliquotted into volumes of 0.5 ml and stored at ≤70° C. Collected samples were subsequently shipped to Prevalere Life Sciences (Rome, N.Y.) on dry ice. Separate aliquots were prepared for analysis of each parameter discussed below (pharmacokinetics, pharmacodynamics, anti-drug antibody, and neutralizing antibody). Samples received at Prevalere were kept at ≤70° C. until analysis.

FP-1039 concentration was measured in plasma from the subjects using a quantitative enzyme immunoassay methodology that measures free, active FP-1039 in $K_2$EDTA plasma. Briefly, samples and controls were diluted in assay diluent containing excess heparin and loaded onto plates pre-coated with recombinant human FGF-2 and pre-blocked. After a 1-hour incubation, the plate was washed and an anti-human IgG-Fc horseradish peroxidase (HRP) antibody added to detect bound FP-1039 using standard colorimetric ELISA detection. The method was validated in accordance with bioanalytical method validation guidelines and following Good Laboratory Practices (GLP) prior to clinical sample testing at Prevalere Life Sciences.

Plasma concentrations vs. time curves were generated. Non-compartmental analysis was performed with WinNonlin professional version 5.2.1 (Pharsight Corporation, Mountain View, Calif.) or PK Solutions 2.0™ software (Version 2.0.6 for Windows, Excel 2002 edition; Summit Research Services, Montrose, Colo.). The area under the curve from time zero to the last measureable time point ($AUC_{0-t}$) was estimated using the trapezoid method. Linear regression over the last three or more time points was used to estimate the elimination rate constant (λ) which was used to estimate terminal half-life ($t_{1/2}$) and AUC from zero to infinity ($AUC_{0-\infty}$) from the following equations:

$$t_{1/2}=\ln(2)/\lambda,$$

$$AUC_{0-\infty}=AUC_{0-t}+C_t/\lambda$$

where $C_t$ is the last measureable concentration. Plasma clearance (CL) was determined from the following equation:

$$CL=\text{Dose}/AUC_{0-\infty}$$

The maximum concentration ($C_{max}$) and the time from the start of infusion of the maximum concentration ($T_{max}$) was determined directly from the data.

As shown in FIG. 1, the mean plasma concentration for each dose cohort along with standard deviation data was plotted against time. The pharmacokinetic profile of FP-1039 was typical of a large protein with an initial distribution phase and a second (terminal/elimination) phase. As shown in FIG. 1, there was a linear, dose-dependent increase in drug exposure in the plasma compartment. At a dose of 8 mg/kg body weight, the individual subject terminal half-life ($t_{1/2}$) ranged from 113 to 120 hours, with the mean of 117 hours (4.9 days) after the fourth dose on Day 22. The pharmacokinetic parameters $C_{max}$, $C_{min}$, and AUC increased in proportion to the dose. As shown in FIG. 1, the plasma concentration of FP-1039 remains above 10 μg/ml even at one week post dosing. Furthermore, there was accumulation of FP-1039 in the plasma when comparing the $C_{max}$, $C_{min}$, and AUC data between the Day 1 and Day 22 doses (first vs. fourth dose). In summary, the pharmacokinetic profile of FP-1039 supports twice weekly, weekly, or less frequent dosing.

Pharmacodynamics

The target engagement of FGF-2 at various doses of FP-1039 was measured at multiple timepoints. Plasma samples were drawn pre-dose (Day 1), 24 hours post first dose (Day 2), and at Day 36 (14 days past 4$^{th}$/last dose).

Plasma free FGF-2 levels were measured using a modified commercial immunoassay kit (Meso Scale Discovery, MSD) which utilizes an electrochemiluminescent (ECL) technology based on paired antibodies for detection of FGF-2. The detection system employs a ruthenium metal chelate (Sulfo-Tag) antibody as the ECL label. The relative mass values for natural FGF-2 in the plasma or serum samples is determined using the recombinant protein standards provided in the kit. Briefly, samples and controls were diluted in assay diluent and loaded onto plates pre-coated with antibodies against FGF-2 and pre-blocked. After a 2-hour incubation, the plate was washed and a detection antibody (SULFO-TAG antihuman growth factor detection antibody blend) was added. After a 2-hour incubation, the plate was washed and read with the MSD SI2400 reader (Meso Scale Discovery, Sector Image 2400, Model #1250) and the data analyzed.

Figure 2:
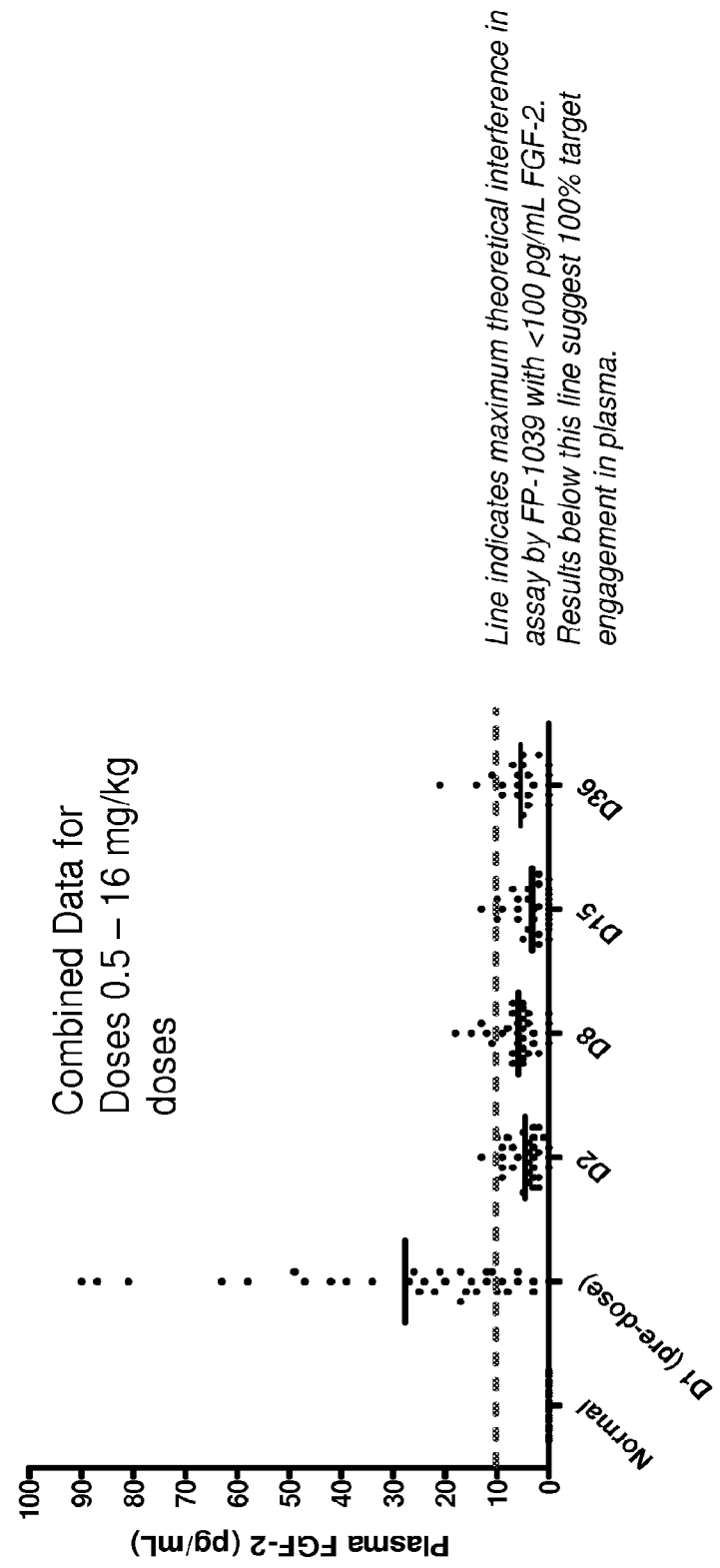
FIG. 2. Summary of plasma free FGF-2 levels at different timepoints across all dosing cohorts (0.5-16 mg/kg). Free FGF-2 was measured pre-dose Day 1, 24-hours post the 1st dose, pre-dose Day 8, Day 15, and Day 36. The Day 36 samples are two weeks following FP-1039 dosing.
Figure 3:
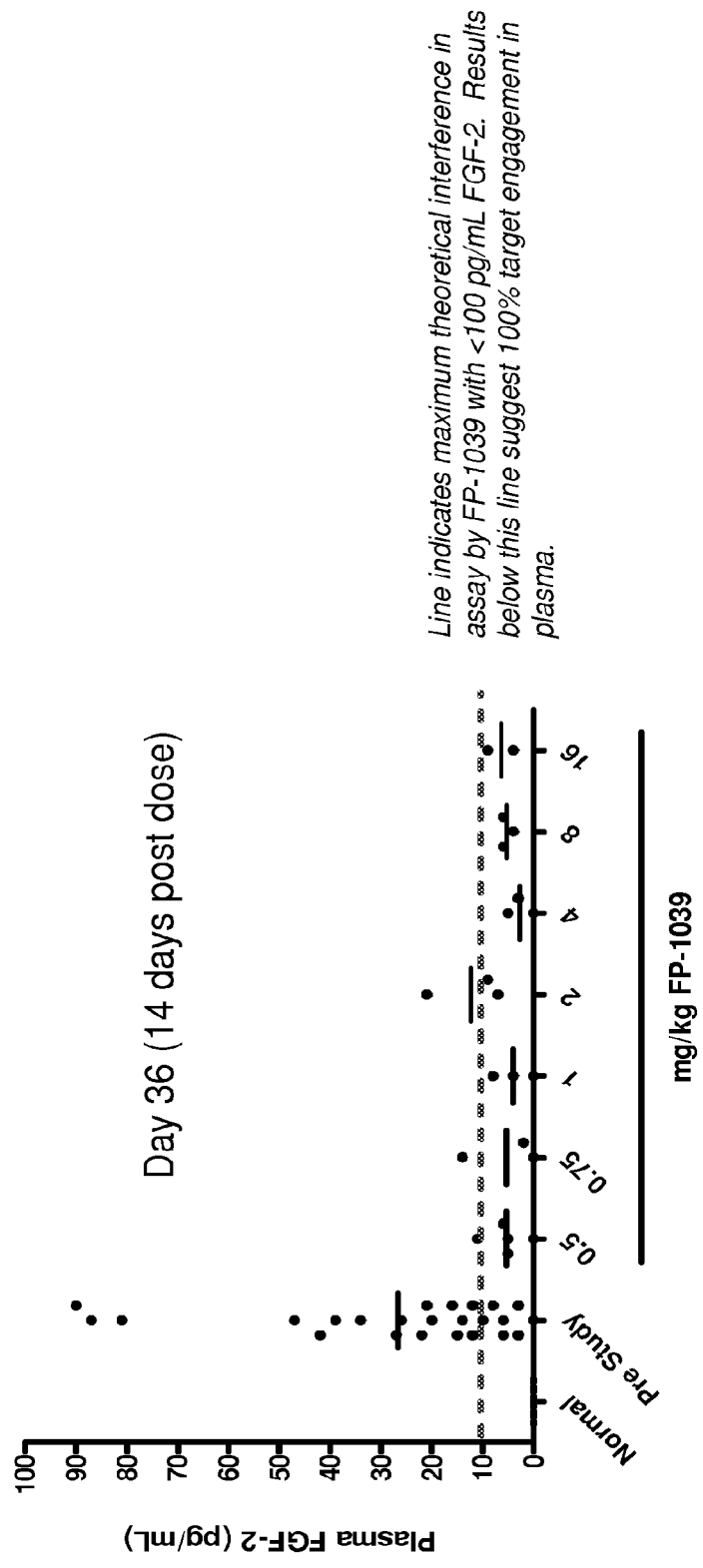
FIG. 3. Free FGF-2 plasma levels in normal subjects and patients before and after a single dose of FP-1039. All patients had elevated FGF-2 plasma levels compared to plasma from normal subjects. Plasma free-FGF-2 levels in cancer patients treated with FP-1039 all decreased relative to pre-dose levels (overall average decrease of 76%).

FGF-2 Levels:

Prior to FP-1039 treatment, clinical subjects had elevated mean FGF-2 plasma concentrations relative to normal donors. As shown in FIGS. 2-3, treatment with FP-1039 results in a decrease in free plasma FGF-2, suggesting that FP-1039 sequesters FGF-2 present in the blood. FIG. 2 shows that within 48 hours post dosing with FP-1039, there is a significant decrease in plasma FGF-2 levels. Among all of the dosing levels shown in FIGS. 2-3, plasma free FGF-2 levels in cancer patients decreased relative to pre-dose levels (overall average decrease of 76%). This data demonstrates that FP-1039 exhibits a high degree of target engagement in plasma. Moreover, target engagement is maintained throughout the dosing schedule of weekly dosing. The data further suggest that target engagement may be maintained even after 2 weeks, supporting less frequent dosing.

Immune Response

To evaluate whether patients developed an immune response to FP-1039, samples were taken on Day 1, Day 15, Day 36, and every 3 months following the initial dose. Antidrug antibodies directed against FP-1039 in the subject plasma samples were analyzed by an electrochemiluminescent immunoassay (ECLA) utilizing Meso Scale Discovery (MSD) technology, which employs a ruthenium metal chelate (Sulfo-Tag) as the ECL label.

Preliminary analysis of anti-drug antibodies demonstrated that approximately 33% of subjects had transient, low titer antibodies at Day 15. There was no relationship of ADAs to PK, target engagement, or safety observations.

```
                        INFORMAL SEQUENCE LISTING

Human FGFR1 isoform IIIc extracellular domain
                                                            SEQ ID NO: 1
RPSPTLPEQ AQPWGAPVEV ESFLVHPGDL LQLRCRLRDD VQSINWLRDG VQLAESNRTR
ITGEEVEVQD SVPADSGLYA CVTSSPSGSD TTYFSVNVSD ALPSSEDDDD DDDSSSEEKE
TDNTKPNPVA PYWTSPEKME KKLHAVPAAK TVKFKCPSSG TPNPTLRWLK NGKEFKPDHR
IGGYKVRYAT WSIIMDSVVP SDKGNYTCIV ENEYGSINHT YQLDVVERSP HRPILQAGLP
ANKTVALGSN VEFMCKVYSD PQPHIQWLKH IEVNGSKIGP DNLPYVQILK TAGVNTTDKE
MEVLHLRNVS FEDAGEYTCL AGNSIGLSHH SAWLTVLEAL EERPAVMTSP LYLE Human FGFR1 isoform IIIc extracellular domain Δ4
                                                            SEQ ID NO: 2
RPSPTLPEQ AQPWGAPVEV ESFLVHPGDL LQLRCRLRDD VQSINWLRDG VQLAESNRTR
ITGEEVEVQD SVPADSGLYA CVTSSPSGSD TTYFSVNVSD ALPSSEDDDD DDDSSSEEKE
TDNTKPNPVA PYWTSPEKME KKLHAVPAAK TVKFKCPSSG TPNPTLRWLK NGKEFKPDHR
IGGYKVRYAT WSIIMDSVVP SDKGNYTCIV ENEYGSINHT YQLDVVERSP HRPILQAGLP
```

INFORMAL SEQUENCE LISTING

```
ANKTVALGSN VEFMCKVYSD PQPHIQWLKH IEVNGSKIGP DNLPYVQILK TAGVNTTDKE
MEVLHLRNVS FEDAGEYTCL AGNSIGLSHH SAWLTVLEAL EERPAVMTSP
```

Human FGFR1 isoform IIIc extracellular domain Δ8
                                                                SEQ ID NO: 3
```
RPSPTLPEQ AQPWGAPVEV ESFLVHPGDL LQLRCRLRDD VQSINWLRDG VQLAESNRTR
ITGEEVEVQD SVPADSGLYA CVTSSPSGSD TTYFSVNVSD ALPSSEDDDD DDDSSSEEKE
TDNTKPNPVA PYWTSPEKME KKLHAVPAAK TVKFKCPSSG TPNPTLRWLK NGKEFKPDHR
IGGYKVRYAT WSIIMDSVVP SDKGNYTCIV ENEYGSINHT YQLDVVERSP HRPILQAGLP
ANKTVALGSN VEFMCKVYSD PQPHIQWLKH IEVNGSKIGP DNLPYVQILK TAGVNTTDKE
MEVLHLRNVS FEDAGEYTCL AGNSIGLSHH SAWLTVLEAL EERPAV
```

Human FGFR1 isoform IIIc extracellular domain Δ9
                                                                SEQ ID NO: 4
```
RPSPTLPEQ AQPWGAPVEV ESFLVHPGDL LQLRCRLRDD VQSINWLRDG VQLAESNRTR
ITGEEVEVQD SVPADSGLYA CVTSSPSGSD TTYFSVNVSD ALPSSEDDDD DDDSSSEEKE
TDNTKPNPVA PYWTSPEKME KKLHAVPAAK TVKFKCPSSG TPNPTLRWLK NGKEFKPDHR
IGGYKVRYAT WSIIMDSVVP SDKGNYTCIV ENEYGSINHT YQLDVVERSP HRPILQAGLP
ANKTVALGSN VEFMCKVYSD PQPHIQWLKH IEVNGSKIGP DNLPYVQILK TAGVNTTDKE
MEVLHLRNVS FEDAGEYTCL AGNSIGLSHH SAWLTVLEAL EERPA
```

Human FGFR1 isoform IIIc extracellular domain Δ14
                                                                SEQ ID NO: 5
```
RPSPTLPEQ AQPWGAPVEV ESFLVHPGDL LQLRCRLRDD VQSINWLRDG VQLAESNRTR
ITGEEVEVQD SVPADSGLYA CVTSSPSGSD TTYFSVNVSD ALPSSEDDDD DDDSSSEEKE
TDNTKPNPVA PYWTSPEKME KKLHAVPAAK TVKFKCPSSG TPNPTLRWLK NGKEFKPDHR
IGGYKVRYAT WSIIMDSVVP SDKGNYTCIV ENEYGSINHT YQLDVVERSP HRPILQAGLP
ANKTVALGSN VEFMCKVYSD PQPHIQWLKH IEVNGSKIGP DNLPYVQILK TAGVNTTDKE
MEVLHLRNVS FEDAGEYTCL AGNSIGLSHH SAWLTVLEAL
```

Human FGFR1 isoform IIIc extracellular domain Δ19
                                                                SEQ ID NO: 6
```
RPSPTLPEQ AQPWGAPVEV ESFLVHPGDL LQLRCRLRDD VQSINWLRDG VQLAESNRTR
ITGEEVEVQD SVPADSGLYA CVTSSPSGSD TTYFSVNVSD ALPSSEDDDD DDDSSSEEKE
TDNTKPNPVA PYWTSPEKME KKLHAVPAAK TVKFKCPSSG TPNPTLRWLK NGKEFKPDHR
IGGYKVRYAT WSIIMDSVVP SDKGNYTCIV ENEYGSINHT YQLDVVERSP HRPILQAGLP
ANKTVALGSN VEFMCKVYSD PQPHIQWLKH IEVNGSKIGP DNLPYVQILK TAGVNTTDKE
MEVLHLRNVS FEDAGEYTCL AGNSIGLSHH SAWLT
```

Engineered human IgG1 Fc domain with C237S mutation
                                                                SEQ ID NO: 7
```
EPKSSDKTHT CPPCPAPELL GGPSVFLFPP KPKDTLMISR TPEVTCVVVD VSHEDPEVKF
NWYVDGVEVH NAKTKPREEQ YSTYRVVSV LTVLHQDWLN GKEYKCKVSN KALPAPIEKT
ISKAKGQPRE PQVYTLPPSR DELTKNQVSL TCLVKGFYPS DIAVEWESNG QPENNYKTTP
PVLDSDGSFF LYSKLTVDKS RWQQGNVFSC SVMHEALHNH YTQKSLSLSP GK
```

Human FGFR1 isoform IIIc extracellular domain Δ14 linked to human
IgG1 Fc domain
                                                                SEQ ID NO: 8
```
RPSPTLPEQAQPWGAPVEVESFLVHPGDLLQLRCRLRDD
VQSINWLRDGVQLAESNRTRITGEEVEVQDSVPADSGLYACVTSSPSGSDTTYFSVNVSD
ALPSSEDDDDDDDSSSEEKETDNTKPNPVAPYWISPEKMEKKLHAVPAAKTVKFKCPSSG
TPNPTLRWLKNGKEFKPDHRIGGYKVRYATWSIIMDSVVPSDKGNYTCIVENEYGSINHT
YQLDVVERSPHRPILQAGLPANKTVALGSNVEFMCKVYSDPQPHIQWLKHIEVNGSKIGP
DNLPYVQILKTAGVNTTDKEMEVLHLRNVSFEDAGEYTCLAGNSIGLSHHSAWLTVLEAL
EPKSSDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK
```

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method of treating a human having a cancer, the method comprising:
   reducing the fibroblast growth factor-2 (FGF-2) plasma concentration of the human below 4 pg/ml for at least one week by administering to the human a soluble fibroblast growth factor receptor 1 (FGFR1) fusion protein at a dose of at least about 2 mg/kg body weight,
   wherein the soluble FGFR1 fusion protein comprises an FGFR1 extracellular domain linked to a Fc polypeptide, and
   wherein the human has a FGF-2 plasma concentration of at least 6 pg/ml prior to administration of the soluble FGFR1 fusion protein; and
   wherein the method further comprises administering at least one chemotherapeutic agent.

2. The method of claim 1, wherein at least one chemotherapeutic agent is selected from docetaxel, paclitaxel, vincristine, carboplatin, cisplatin, oxaliplatin, doxorubicin, 5-fluorouracil (5-FU), leucovorin, pemetrexed, etoposide, irinotecan, topotecan, and an aromatase inhibitor.

3. The method of claim 1, wherein at least one chemotherapeutic agent is selected from docetaxel, paclitaxel, and carboplatin.

4. The method of claim 1, wherein the method comprises reducing the FGF-2 plasma concentration of the human below 4 pg/ml for at least two weeks.

5. The method of claim 1, wherein the method comprises reducing the FGF-2 plasma concentration of the human below 4 pg/ml as determined by an electrochemiluminescence assay, and wherein the human has FGF-2 plasma concentration of at least 6 pg/ml prior to administration of the soluble FGFR1 fusion protein as determined by an electrochemiluminescence assay, wherein the electrochemiluminescence assay utilizes an anti-FGF-2 antibody as the primary antibody and a ruthenium metal chelate anti-human growth factor antibody blend as the secondary antibody.

6. The method of claim 1, wherein the FGFR1 extracellular domain comprises the amino acid sequence of SEQ ID NO:5.

7. The method of claim 1, wherein the soluble FGFR1 fusion protein comprises the amino acid sequence of SEQ ID NO:8.

8. The method of claim 1, wherein the soluble FGFR1 fusion protein is administered at a dose of about 2 mg/kg body weight to about 20 mg/kg body weight.

9. The method of claim 8, wherein the soluble FGFR1 fusion protein is administered at a dose of about 8 mg/kg body weight to about 16 mg/kg body weight.

10. The method of claim 9, wherein the soluble FGFR1 fusion protein is administered at a dose of about 8 mg/kg body weight.

11. The method of claim 9, wherein the soluble FGFR1 fusion protein is administered at a dose of about 16 mg/kg body weight.

12. The method of claim 1, wherein the cancer is prostate cancer, breast cancer, colorectal cancer, lung cancer, endometrial cancer, head and neck cancer, laryngeal cancer, liver cancer, renal cancer, glioblastoma, or pancreatic cancer.

13. The method of claim 1, wherein the human has an FGF-2 plasma concentration of at least 10 pg/ml prior to the administration of the soluble FGFR1 fusion protein, wherein the FGF-2 plasma concentration is determined according to an electrochemiluminescence assay, which utilizes an anti-FGF-2 antibody as the primary antibody and a ruthenium metal chelate anti-human growth factor antibody blend as the secondary antibody.

14. The method of claim 1, wherein the soluble FGFR1 fusion protein is administered by intravenous infusion.

15. The method of claim 14, in which the intravenous infusion is over a period of 30 minutes.

16. The method of claim 12, wherein the cancer is prostate cancer, breast cancer, colorectal cancer, lung cancer, endometrial cancer, head and neck cancer, laryngeal cancer, liver cancer, renal cancer, glioblastoma, or pancreatic cancer.

17. A method of treating a human having a cancer, the method comprising:
   reducing the fibroblast growth factor-2 (FGF-2) plasma concentration of the human below 4 pg/ml for at least one week by administering to the human a soluble fibroblast growth factor receptor 1 (FGFR1) fusion protein at a dose of at least about 2 mg/kg body weight,
   wherein the soluble FGFR1 fusion protein comprises an FGFR1 extracellular domain linked to a Fc polypeptide, and
   wherein the human has a FGF-2 plasma concentration of at least 6 pg/ml prior to administration of the soluble FGFR1 fusion protein; and
   wherein the method further comprises administering at least one VEGF antagonist.

18. The method of claim 17, wherein the VEGF antagonist is selected from a VEGF antibody and a VEGF trap.

19. The method of claim 18, wherein the VEGF antagonist is a VEGF antibody.

20. The method of claim 19, wherein the VEGF antibody is bevacizumab.

21. The method of claim 18, wherein the VEGF antagonist is a VEGF trap.

22. The method of claim 21, wherein the VEGF trap is aflibercept.

23. The method of claim 17, wherein the VEGF antagonist is selected from sorafenib and sunitinib.

24. The method of claim 17, wherein the method comprises reducing the FGF-2 plasma concentration of the human below 4 pg/ml for at least two weeks.

25. The method of claim 17, wherein the method comprises reducing the FGF-2 plasma concentration of the human below 4 pg/ml as determined by an electrochemiluminescence assay, and wherein the human has FGF-2 plasma concentration of at least 6 pg/ml prior to administration of the soluble FGFR1 fusion protein as determined by an electrochemiluminescence assay, wherein the electrochemiluminescence assay utilizes an anti-FGF-2 antibody as the primary antibody and a ruthenium metal chelate anti-human growth factor antibody blend as the secondary antibody.

26. The method of claim 17, wherein the FGFR1 extracellular domain comprises the amino acid sequence of SEQ ID NO:5.

27. The method of claim 17, wherein the soluble FGFR1 fusion protein comprises the amino acid sequence of SEQ ID NO:8.

28. The method of claim 17, wherein the soluble FGFR1 fusion protein is administered at a dose of about 2 mg/kg body weight to about 20 mg/kg body weight.

29. The method of claim 17, wherein the soluble FGFR1 fusion protein is administered at a dose of about 8 mg/kg body weight to about 16 mg/kg body weight.

30. The method of claim 29, wherein the soluble FGFR1 fusion protein is administered at a dose of about 8 mg/kg body weight.

31. The method of claim 29, wherein the soluble FGFR1 fusion protein is administered at a dose of about 16 mg/kg body weight.

* * * * *